United States Patent
Mott et al.

(10) Patent No.: US 7,274,956 B2
(45) Date of Patent: *Sep. 25, 2007

(54) CONNECTOR FOR INTERFACING INTRAVASCULAR SENSORS TO A PHYSIOLOGY MONITOR

(75) Inventors: Eric V. Mott, Rancho Cordova, CA (US); T. Sean Winterer, Placerville, CA (US)

(73) Assignee: Volcano Corporation, Rancho Cordova, CA (US)

( * ) Notice: Subject to any disclaimer, the term of this patent is extended or adjusted under 35 U.S.C. 154(b) by 756 days.

This patent is subject to a terminal disclaimer.

(21) Appl. No.: 10/691,721

(22) Filed: Oct. 22, 2003

(65) Prior Publication Data

US 2004/0082866 A1    Apr. 29, 2004

Related U.S. Application Data

(63) Continuation of application No. 10/086,143, filed on Feb. 27, 2002, now Pat. No. 6,663,570.

(51) Int. Cl.
- *H01R 13/62* (2006.01)
- *H01R 24/04* (2006.01)
- *A61B 5/04* (2006.01)
- *A61B 5/00* (2006.01)

(52) U.S. Cl. .................. 600/372; 600/300; 439/304; 439/668; 439/909

(58) Field of Classification Search ............... 600/372; 439/909, 669
See application file for complete search history.

(56) References Cited

U.S. PATENT DOCUMENTS

| | | |
|---|---|---|
| 4,684,193 A | 8/1987 | Havel |
| 4,850,358 A | 7/1989 | Millar |
| 4,856,529 A | 8/1989 | Segal |
| 4,869,263 A | 9/1989 | Segal et al. |
| 4,947,852 A | 8/1990 | Nassi et al. |
| 5,059,851 A | 10/1991 | Corl et al. |
| 5,085,223 A | 2/1992 | Lars et al. |
| 5,105,818 A | 4/1992 | Christian et al. |
| 5,121,749 A | 6/1992 | Nassi et al. |
| 5,125,058 A | 6/1992 | Tenerz et al. |
| 5,178,159 A | 1/1993 | Christian |
| 5,195,375 A | 3/1993 | Tenerz et al. |
| 5,226,423 A | 7/1993 | Tenerz et al. |
| 5,271,404 A | 12/1993 | Corl et al. |
| 5,348,481 A | 9/1994 | Ortiz |

(Continued)

OTHER PUBLICATIONS

U.S. Appl. No. 09/861,464, filed May 18, 2001, Dorando et al.

*Primary Examiner*—Charles A. Marmor, II
*Assistant Examiner*—Patricia C Mallari
(74) *Attorney, Agent, or Firm*—O'Melveny & Myers LLP

(57) ABSTRACT

A connector for connecting a flexible elongate member having a sensor mounted thereon to a physiology monitor includes a housing, an electrical contact member disposed within the housing, the electrical contact member having a plurality of axially spaced contact members, a cable having a plurality of conductors being electrically connected to respective axially spaced contact members, and a sleeve having an opening therein which communicates with an internal passage of the housing. The sleeve is moveable between an open position and a closed position. An interlock mechanism may also be provided to prevent the sleeve from moving from the open position to the closed position.

10 Claims, 14 Drawing Sheets

U.S. PATENT DOCUMENTS

| | | |
|---|---|---|
| 5,354,326 A | 10/1994 | Comben |
| 5,358,409 A | 10/1994 | Obara |
| 5,413,508 A * | 5/1995 | Obara ......................... 439/729 |
| 5,482,038 A * | 1/1996 | Ruff ........................... 600/372 |
| 5,651,373 A | 7/1997 | Mah |
| 5,668,320 A | 9/1997 | Cowan |
| RE35,648 E | 11/1997 | Tenerz et al. |
| 5,694,946 A | 12/1997 | Tenerz et al. |
| 5,797,856 A | 8/1998 | Frisbie et al. |
| 5,908,385 A | 6/1999 | Chechelski et al. |
| 5,938,624 A | 8/1999 | Akerfeldt et al. |
| 6,089,103 A | 7/2000 | Smith |
| 6,090,052 A | 7/2000 | Akerfeldt et al. |
| 6,106,476 A | 8/2000 | Corl et al. |
| 6,106,486 A | 8/2000 | Tenerz et al. |
| 6,112,120 A | 8/2000 | Correas |
| 6,112,598 A | 9/2000 | Tenerz et al. |
| 6,142,958 A | 11/2000 | Hammarstrom et al. |
| 6,167,763 B1 | 1/2001 | Tenerz et al. |
| 6,182,513 B1 | 2/2001 | Stemme et al. |
| 6,196,980 B1 | 3/2001 | Akerfeldt et al. |
| 6,210,339 B1 | 4/2001 | Kiepen et al. |
| 6,248,083 B1 | 6/2001 | Smith et al. |
| 6,265,792 B1 | 7/2001 | Granchukoff |
| 6,298,255 B1 | 10/2001 | Cordero et al. |
| 6,336,906 B1 | 1/2002 | Hammarstrom et al. |
| 6,343,514 B1 | 2/2002 | Smith |
| 6,348,035 B1 | 2/2002 | Takami |
| 6,409,677 B1 | 6/2002 | Tulkki |
| 6,415,168 B1 * | 7/2002 | Putz ........................... 600/378 |
| 6,428,336 B1 | 8/2002 | Akerfeldt |
| 6,663,570 B2 * | 12/2003 | Mott et al. ................... 600/486 |
| 2002/0043113 A1 | 4/2002 | Tulkki et al. |

* cited by examiner

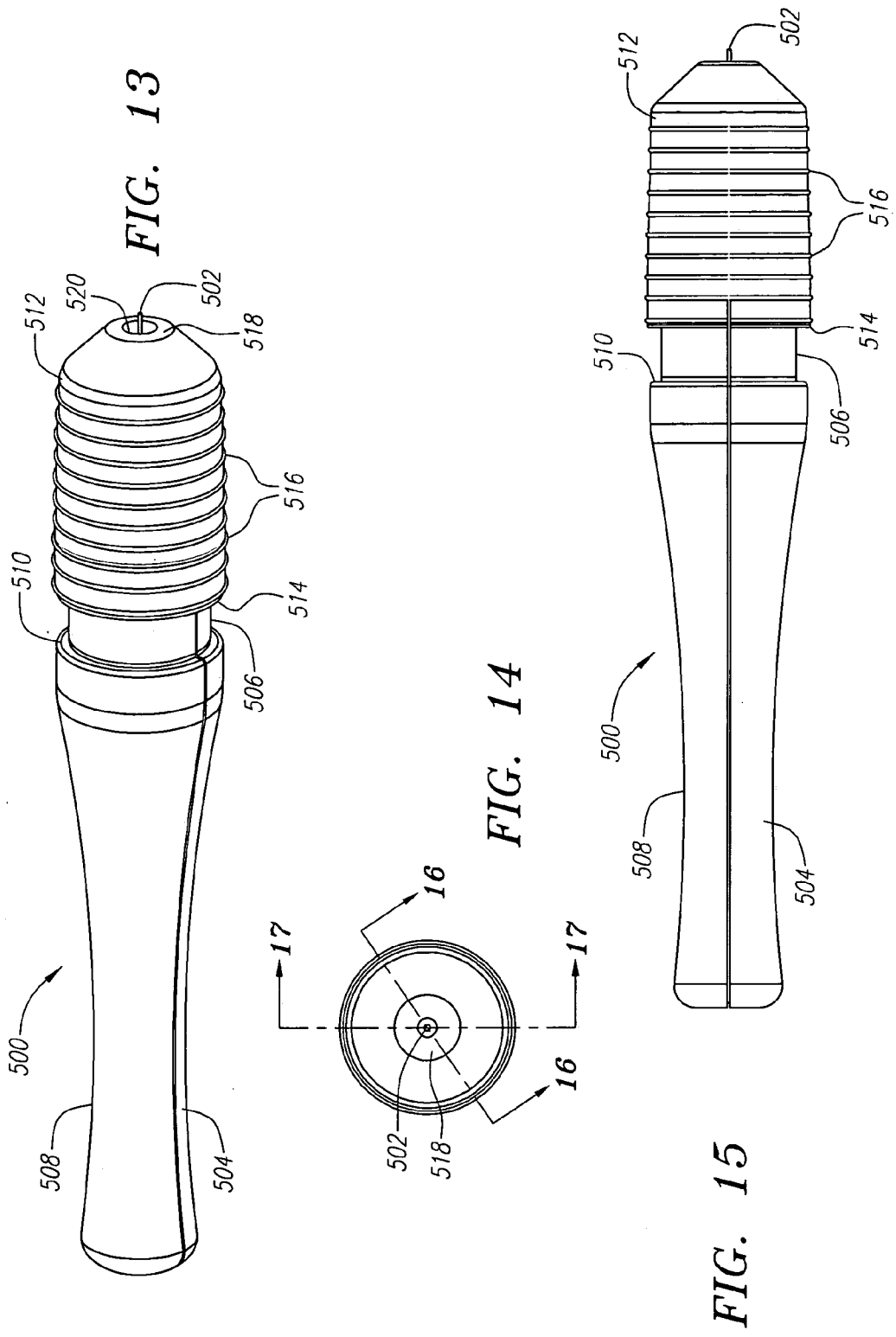

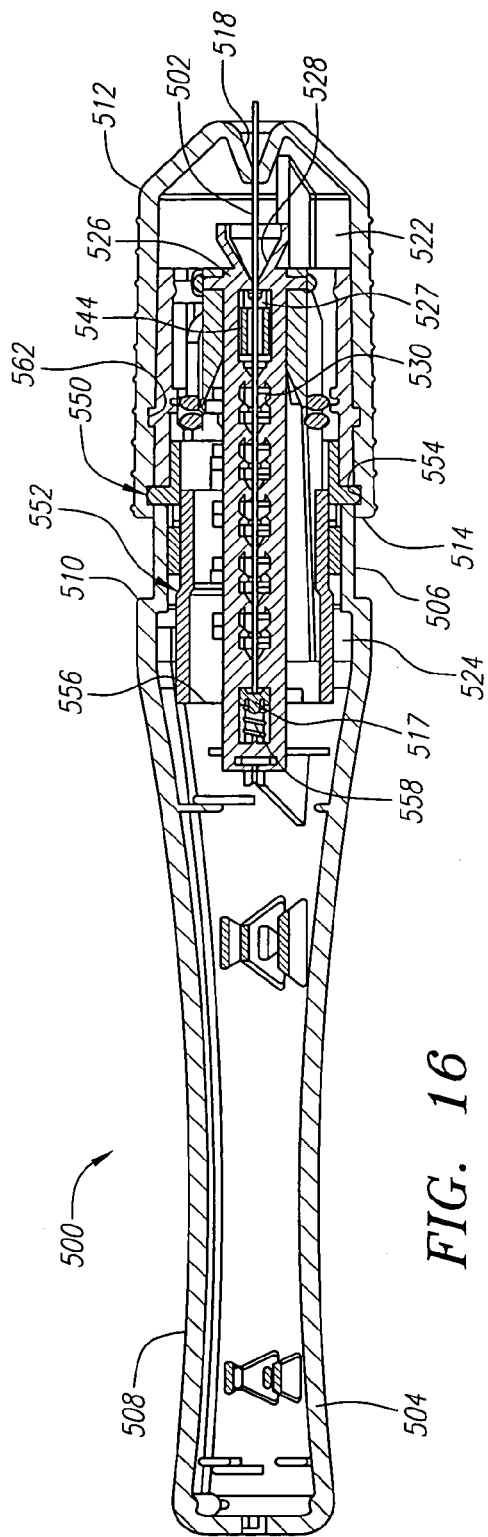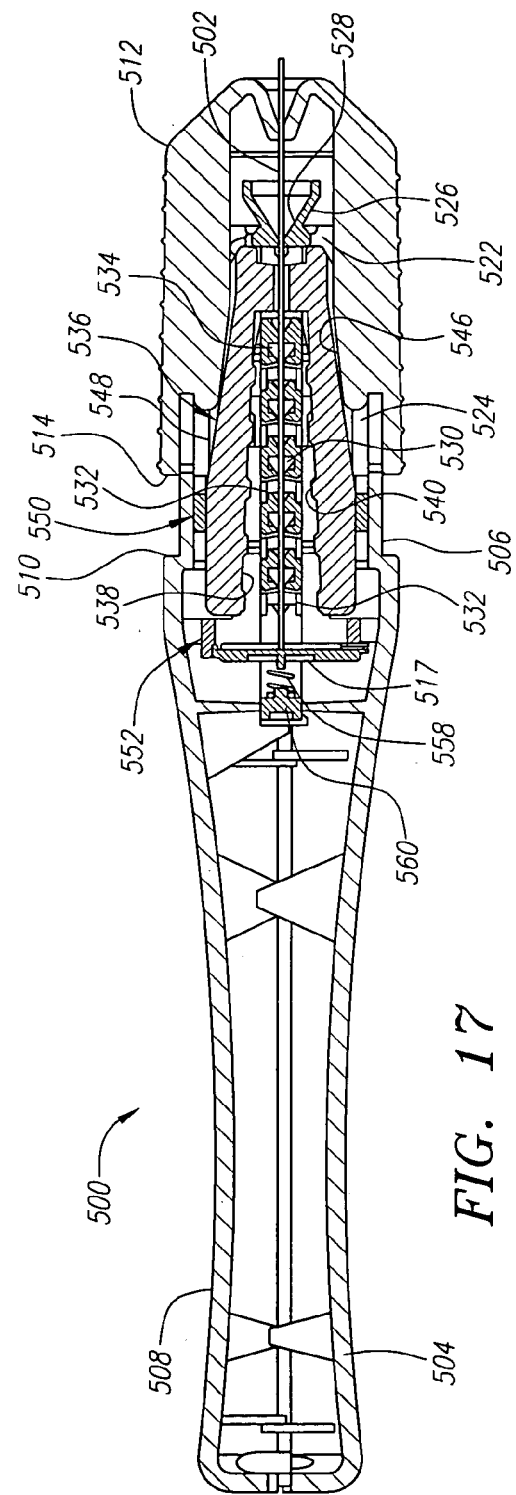

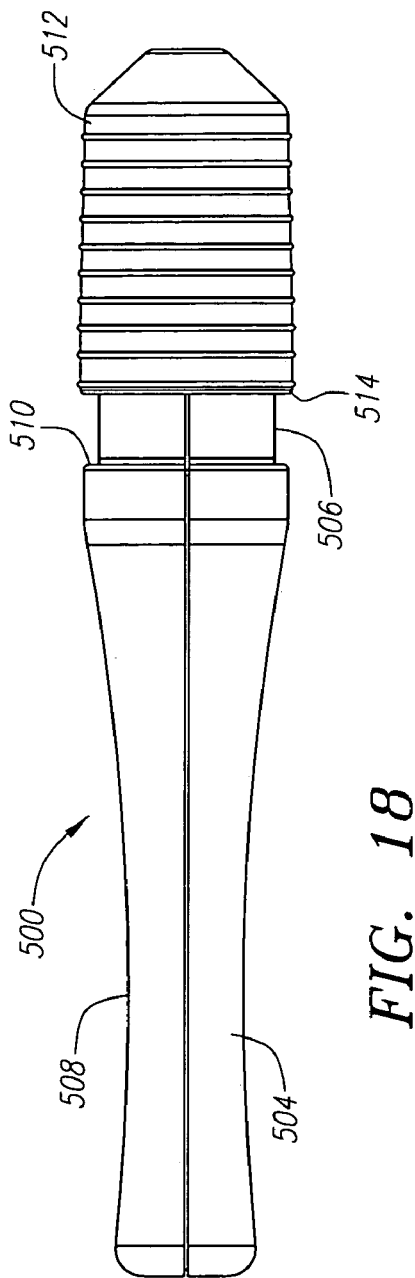
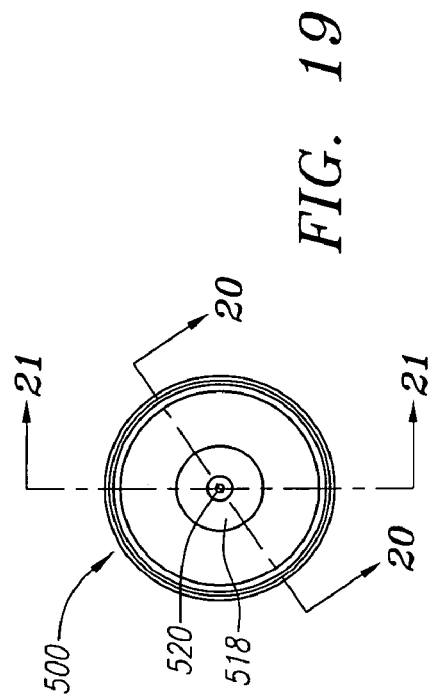
FIG. 18
FIG. 19

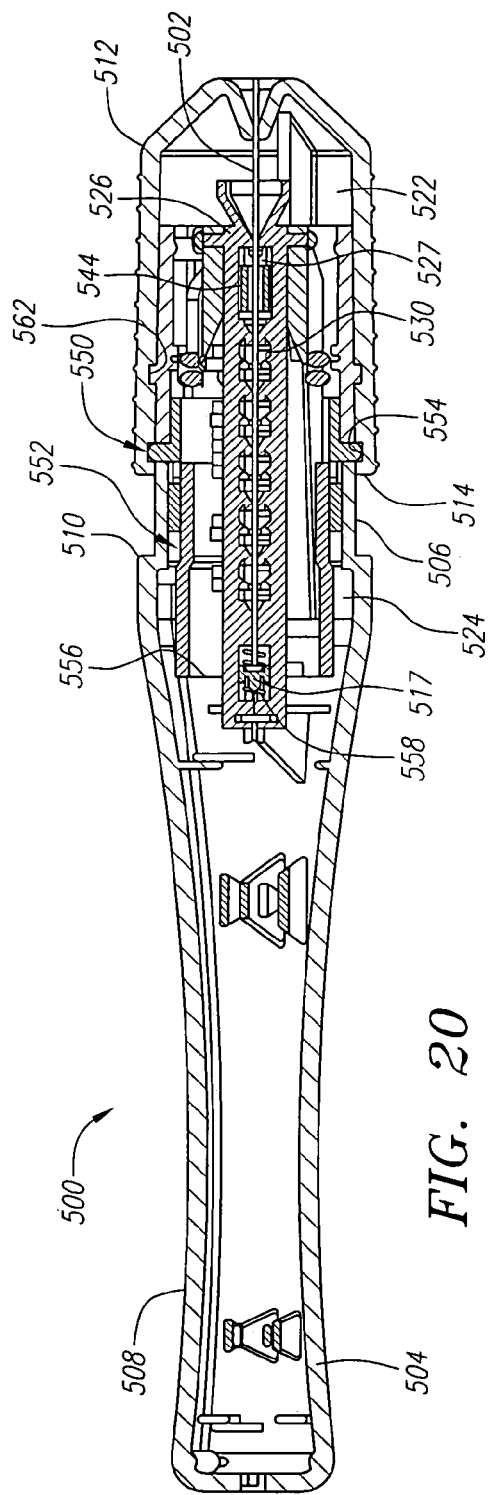
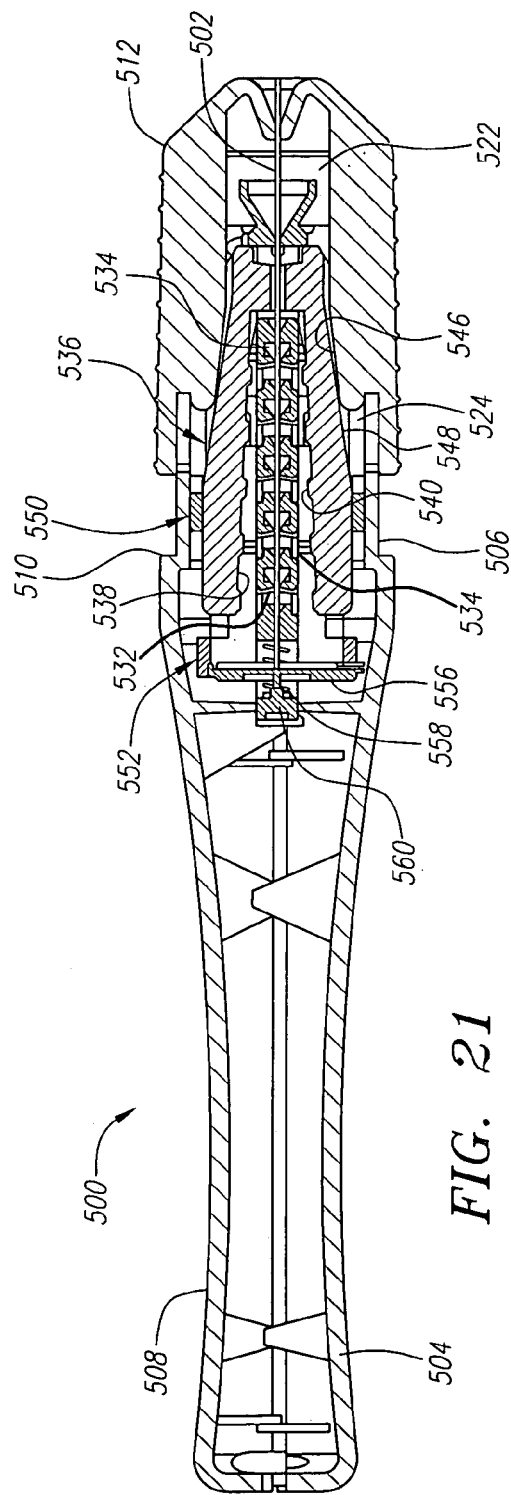

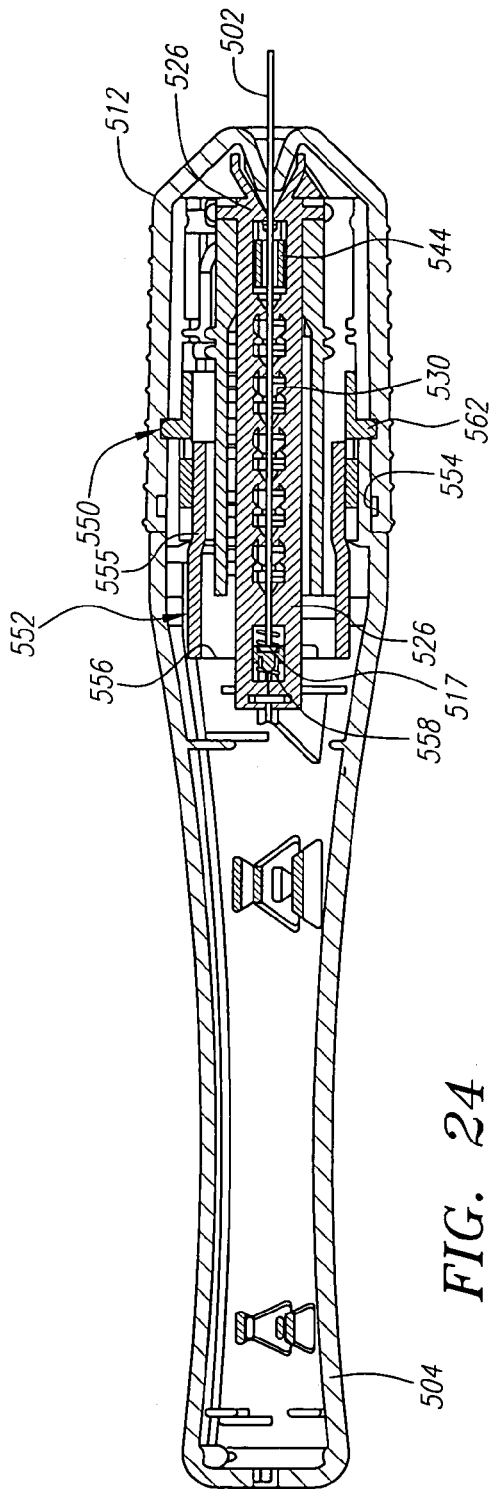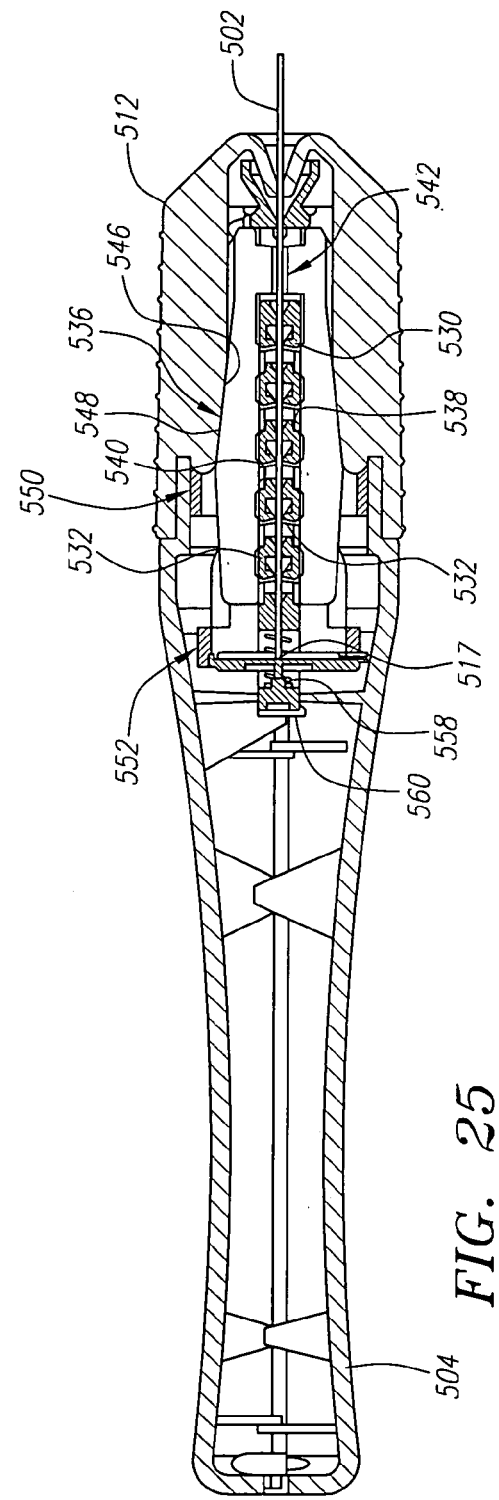

CONNECTOR FOR INTERFACING INTRAVASCULAR SENSORS TO A PHYSIOLOGY MONITOR

RELATED APPLICATION

This Application is a continuation of U.S. application Ser. No. 10/086,143, filed Feb. 27, 2002 now U.S. Pat. Ser. No. 6,663,570, now allowed. The '143 Application is incorporated herein by reference as if set forth fully herein.

FIELD OF THE INVENTION

The present invention generally relates to the area of diagnostic medical equipment, and more particularly to diagnostic devices for identifying problematic blockages within coronary arteries by means of a sensor mounted upon the end of a flexible elongate member such as a guide wire.

BACKGROUND OF THE INVENTION

In the past decade, innovations in the diagnosis of cardiovascular disease have migrated from external imaging processes to internal, catheterization-based, diagnostic processes. Diagnosis of cardiovascular disease has been performed through angiogram imaging wherein a radiopaque dye is injected into a vasculature and a live x-ray image is taken of the portions of the cardiovascular system of interest. Magnetic resonance imaging (MRI) has also been utilized as well. More recently, however, diagnostic equipment and processes have been developed for diagnosing vasculature blockages and other vasculature disease by means of ultra-miniature sensors placed upon a distal end of a flexible elongate member such as a catheter, or a guide wire used for catheterization procedures.

One such ultra-miniature sensor device is a pressure sensor mounted upon the distal end of a guide wire. An example of such a pressure sensor is provided in Corl et al. U.S. Pat. No. 6,106,476, the teachings of which are expressly incorporated herein by reference in their entirety. Such intravascular pressure sensor measures blood pressure at various points within the vasculature to facilitate locating and determining the severity of stenoses or other disruptors of blood flow within the vessels of the human body. Such devices are commonly used to determine the effectiveness of an angioplasty procedure by placing the pressure sensor proximate a stenosis and measuring a pressure difference indicating a partial blockage of the vessel.

As one can imagine, the aforementioned intravascular pressure sensors are utilized in operating room environments including many types of sensors and equipment for diagnosing and treating cardiovascular disease. Clearly, the room for error is very limited. Therefore, there is substantial interest in simplifying every aspect of the operating room to reduce the incidence of errors.

In a known prior intravascular pressure sensor-to-physiological monitor interface arrangement, marketed by JOMED Inc. of Rancho Cordova, Calif., and depicted in FIG. 1, a signal conditioning interface, comprising an amplifier module 10 (e.g., the Model 7000 Patient Cable) and a WAVEMAP processor box 12, is interposed between a physiology monitor 14 and a WAVEWIRE pressure sensing guide wire 16. The guide wire 16 is a disposable device connected via a connector 15 to the amplifier module 10. The amplifier module 10 receives power and an excitation signal through two separate and distinct electrically conductive lines within cable 17 connected to distinct output leads of the WAVEMAP processor box 12. The WAVEMAP processor box receives power from a standard wall outlet 18 via a standard three-pronged (grounded) power cord 20 plugged into the wall outlet 18. Though not shown in the drawing, the physiology monitor is powered via standard AC wall outlet power as well.

The WAVEMAP processor box 12 includes a separate and distinct signal interface connected to the physiology monitor 14. The WAVEMAP processor box receives a differential voltage excitation signal (either AC or DC) from the physiology monitor 14 via a cable 22. The excitation signal transmitted via the cable 22 is considerably lower power than the AC power deliverable to the WAVEMAP processor box 12 from the wall outlet 18 via the power cord 20. The cable 22 also transmits a signal representing sensed pressure (5 microvolts/mmHG) from the WAVEMAP processor box 12 to the physiology monitor 14. Yet another cable 24 transmits an aortic pressure (Pa) sensed by another device, from the physiology monitor 14 to the WAVEMAP processor box 12. The arrangement illustrated in FIG. 1 utilizes a rotary connector such as described in U.S. Pat. Nos. 5,348,481 and 5,178,159 to connect the guide wire to the amplifier module. This type of rotary connector is awkward to manipulate and requires high insertion forces to place the guide wire in the connector.

SUMMARY OF THE INVENTION

In one aspect of the invention, a connector for connecting a flexible elongate member having a sensor mounted thereon to a physiology monitor includes a housing having an internal passage therein, an electrical contact member disposed in the internal passage, the electrical contact member having a plurality of axially spaced contact members, a cable having a plurality of conductors being electrically connected to respective axially spaced contact members, and a sleeve having an opening therein which communicates with the internal passage in the housing and being moveable between an open position and a closed position. An interlock mechanism is disposed in the housing having a locked position and an unlocked position, the interlock mechanism being in an unlocked position when an end of the flexible elongate member is fully inserted into the connector, the interlock mechanism being moveable between the locked position and the unlocked position by movement of the sleeve, wherein the interlock mechanism is in the locked position, the sleeve is prevented from moving from the open to the closed position.

In another aspect of the invention, a connector for connecting a flexible elongate member having a sensor mounted thereon to a physiology monitor includes a housing having an internal passage therein, an engagement member disposed in the internal passage, the engagement member being moveable between an engaged position and a disengaged position, wherein the engagement member grips the flexible elongate member in the engaged position, and a sleeve having an opening therein which communicates with the internal passage in the housing and being moveable between an open position and a closed position, wherein when the sleeve is in the closed position, the engagement member is in the engaged position. An interlock mechanism is disposed in the housing having a locked position and an unlocked position, the interlock mechanism being in an unlocked position when an end of the flexible elongate member is fully inserted into the connector, the interlock mechanism being moveable between the locked position and the unlocked position by movement of the sleeve, wherein the interlock mechanism is in the locked position, the sleeve is prevented from moving from the open to the closed position.

In still another aspect of the invention, a connector for connecting a flexible elongate member having a sensor mounted thereon to a physiology monitor includes a housing having an internal passage therein, an electrical contact member disposed in the internal passage, the electrical contact member having a plurality of axially spaced contact members, a cable having a plurality of conductors being electrically connected to respective axially spaced contact members, an engagement member disposed in the internal passage, the engagement member being moveable between an engaged position and a disengaged position, wherein the engagement member grips the flexible elongate member in the engaged position, and a sleeve having an opening therein which communicates with the internal passage in the housing and being moveable between an open position and a closed position, wherein when the sleeve is in the closed position, the engagement member is in the engaged position.

Other objects and features of the present invention will become apparent from consideration of the following description taken in conjunction with the accompanying drawings.

BRIEF DESCRIPTION OF THE DRAWINGS

While the appended claims set forth the features of the present invention with particularity, the invention, together with its objects and advantages, may be best understood from the following detailed description taken in conjunction with the accompanying drawings of which:

FIG. 13 is a perspective view of an illustrative connector for connecting to the guide wire constructed in accordance with another aspect of the present invention showing the connector in an open position.

FIG. 14 is an end view of the connector of FIG. 13.

FIG. 15 is a side elevation view of the connector of FIG. 13 showing the connector in the open and locked position.

FIG. 16 is a cross-sectional view taken along the line 16-16 in FIG. 14 showing the connector in the open and locked position.

FIG. 17 is a cross sectional view taken along the line 17-17 in FIG. 14 showing the connector in the open and locked position.

FIG. 18 is a side elevation view of the connector of FIG. 13 showing the connector in the open and unlocked position.

FIG. 19 is an end view of the connector of FIG. 18.

FIG. 20 is a cross-sectional view taken along the line 20-20 in FIG. 19 showing the connector in the open and unlocked position.

FIG. 21 is a cross-sectional view taken along the line 21-21 in FIG. 19 showing the connector in the open and unlocked position.

FIG. 24 is a cross-sectional view taken along the line 24-24 in FIG. 23 showing the connector in the closed position.

FIG. 25 is a cross-sectional view taken along the line 25-25 in FIG. 23 showing the connector in the closed position.

DETAILED DESCRIPTION OF THE PREFERRED EMBODIMENTS

Figure 2:
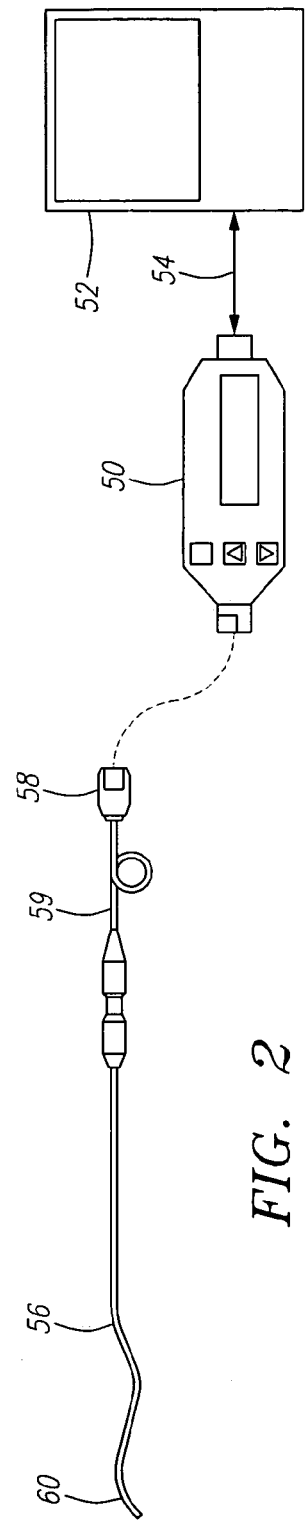
FIG. 2 is a schematic drawing depicting an exemplary connection scheme between a diagnostic pressure sensing guide wire and a physiology monitor in accordance with the present invention.

In general, an exemplary signal conditioning device embodying the present invention, described herein below with respect to FIG. 2, is designed to interface a guide wire-mounted pressure sensor to a standard physiology (e.g., blood pressure) monitor. The signal conditioning device processes a signal received from the guide wire-mounted pressure sensor and presents a normalized signal to any of multiple different physiology monitors having potentially differing signal requirements.

From the point of view of overall system setup, the exemplary signal conditioning device reduces the number of power sources, as well as the distinct cables and physically distinct apparatuses, required to conduct intravascular blood pressure measurements. These desirable attributes are achieved by having the conditioning device receive and/or utilize a differential sensor excitation signal, transmitted by known physiology monitors in a novel manner.

Known signal conditioning devices utilize the excitation signal as a reference voltage for generating an output signal scaled according to a sensed pressure. However, in the exemplary signal conditioning device, a rectifying, AC to DC converting, power supply circuit draws current from the received excitation signal. The drawn current powers a processor, smaller-scale integrated circuits and discrete circuit elements that perform signal generating/amplifying/conditioning functions within the signal conditioning device. Such functions include driving output current to a polysilicon pressure sensor mounted upon a guide wire. An example of such a polysilicon pressure sensor is disclosed in Corl et al. U.S. Pat. No. 6,106,476, the contents of which are incorporated herein by reference in their entirety including any references contained therein. The signal conditioning device, by way of example, drives an output signal to physiology monitors having a sensitivity of about 5 microVolts per Volt(input)/mmHg. The signal conditioning device also drive an LCD display showing the high and low sensed pressures during a two-second interval.

As in prior signal conditioning interface circuits, a portion of the input excitation signal from the physiology monitor drives (i.e., provides a voltage reference for) a differential voltage output signal transmitted by the signal conditioning device to the physiology monitor representing a sensed pressure. The differential voltage output signal is, for example, generated by a pair of digital-to-analog converters. The generated differential voltage output signal generally comprises a base (i.e., reference) differential voltage signal corresponding to the input differential signal from the physiology monitor. The reference differential voltage is multiplied by a scalar value, representing the sensed and conditioned (e.g., filtered) pressure value provided by the signal conditioning device's processor. Thus, the disclosed embodiment of the present invention accomplishes signal generating, conditioning and amplification without reliance upon a separate signal source to provide DC power to the signal conditioning device's circuits.

With reference now to FIG. 2, a signal conditioning device 50 embodying the present invention connects to a physiology monitor 52 via a five line connector cable 54. The five line connector cable 54 includes a pair of excitation signal lines driven by the physiology monitor 52. The excitation signal lines are driven as a differential voltage pair at, by way of example, 2.4-11 Vdc, 2.4-8 Vrms sine wave (1 kHz to 5 kHz), or 2.4-8 Vrms square wave (dc to 5 kHz). The sine wave input has a more limited range due to the droop between peak voltages at lower frequencies. The rectified square wave has very little gap, and droop is thus a non-issue.

In an embodiment of the invention, electronic components of the signal conditioning device 50 are powered by current drawn from the excitation signal supplied on the excitation signal lines of cable 54. Though not present in the exemplary embodiment of the invention, in alternative embodiments the signal conditioning device includes a battery as a supplementary/backup power source when power from an outside source is either insufficient or not available for the signal conditioning device 50. In a preferred embodiment, no battery is present because the signal conditioning device 50's design enables the device 50 to operate on less than about 20 mA rms, and such power requirements are met by physiology monitors that meet the Association for the Advancement of Medical Instrumentation ("AAMI") standard for Sensor Excitation Power. Examples of physiology monitors 50 meeting the above power requirements may include: all hemodynamic instruments with pressure sensor ports meeting American National Standards Institute ("ANSI")/AAMI BP22-1994; models RM-6000, RMC-2000, RMC-3100, Lifescope-S, RMC-1100, marketed by Nihon Kohden America, Inc. of Foothill Ranch, Calif.; models EP-1102 and EP-1600, marketed by the NEC Corporation of Tokyo, Japan; and models MCS-5500, MCS-7000, DS-3300, marketed by Fukuda Denshi of Tokyo, Japan.

The five line connector cable 54 includes a pair of differential output signal lines. The output signal lines are driven by the signal conditioning device 50's output digital to analog converters (discussed further herein below). The differential output signal, by way of example, operates at 5 microV per volt/mmHG. An operating range of −150 microV/V to 1650 microV/V therefore represents a sensed pressure range of −30 to 330 mmHg. An exemplary resolution (minimum step) for the differential output signal is 0.2 mmHg.

Figure 1:
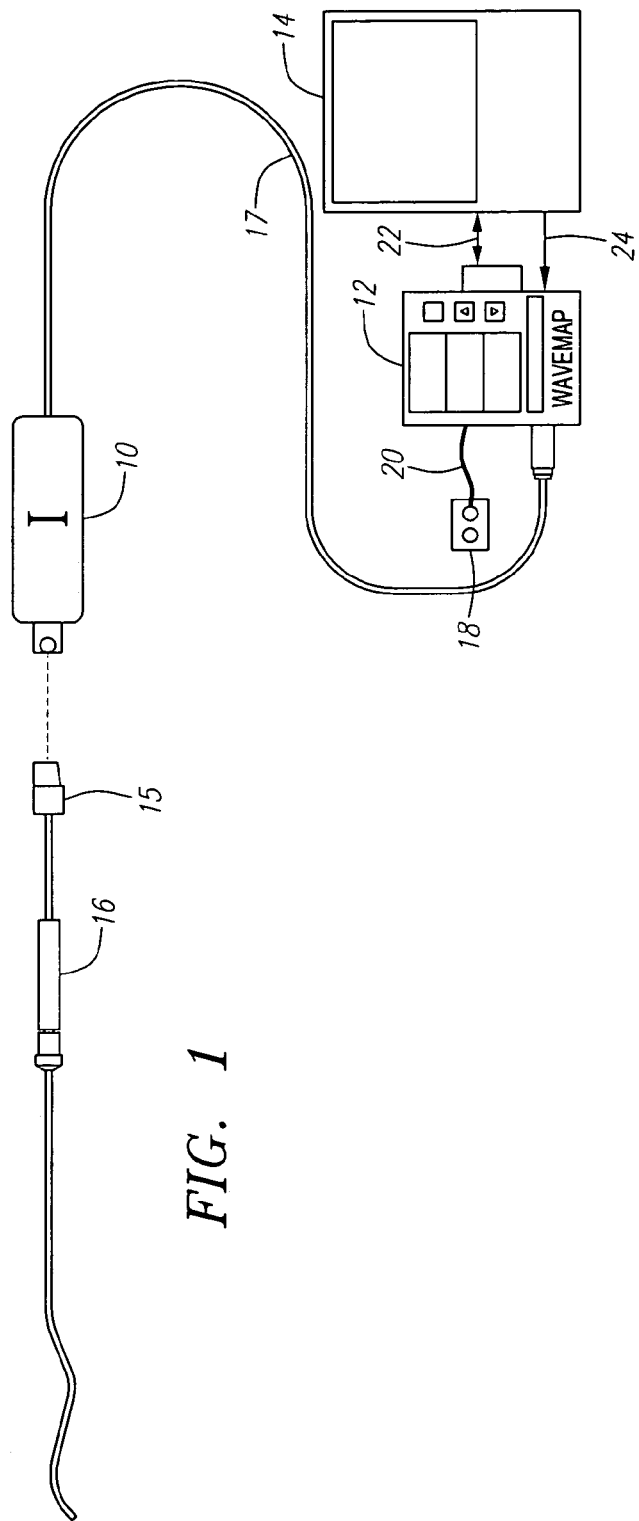
FIG. 1 is a schematic drawing depicting a prior connection scheme between a diagnostic pressure sensing guide wire and a physiology monitor.

The fifth line of the five line connector cable 54 carries a ground signal. Thus, all signal/power requirements for the signal conditioning device 50 are met by the standard five-line output of the physiology monitor 52. Thus, the need for any interface device (such as the processor box 12 of FIG. 1) is eliminated, and the pressure sensing system set-up complexity is reduced.

On the patient side, the signal conditioning device 50 couples to a replaceable guide wire 56 via a connector 58 and corresponding static cable 59, which in turn connects to the guide wire 56 via a static connector 500. The connector 58 couples a set of ten lines in the static cable 59 carrying signals between the replaceable guide wire 56 and the signal conditioning device 50. A first set of five lines of the connector 58 is utilized to generate and receive pressure sensor-related signals. A second set of five lines of the connector 58 concerns an interface to a guide wire sensor's characterization electrically erasable programmable read-only memory ("EEPROM") mounted on the static cable 59 that stores a set of values relating to characteristics of a mounted sensor.

With regard to the second set of five lines of the connector 58, four of the five lines (the fifth line is not used) of the ten-line connector 58 facilitate reading characterization data from an EEPROM carried on the static cable for a guide wire-mounted sensor device 60, which is by way of example a pressure sensor. The EEPROM includes temperature compensation, gain, and offset values used by the signal conditioning device 50 to process the sensed signals from the sensor device 60. A power and ground line are provided by the signal conditioning device 50 to the EEPROM via the connector 58. A clock and data line for reading the EEPROM's data make up the final two lines.

The first set of five lines associated with the connector 58 includes a voltage reference line that is, by way of example, connected to each of two pressure sensing polysilicon resistive sensor elements on guide wire-mounted pressure sensor 60. The remaining four lines comprise two sets of excite/sense signal pairs. In an embodiment of the invention, a first current flows on a first, shorted, excite/sense pair of lines. A second current, separately adjustable with regard to the first current, flows on a second, shorted, excite/sense pair of lines of the connector 58. In the configuration of FIG. 2, the first and second currents pass through the first and second resistive sensor elements of the pressure sensor 60 mounted upon the distal end of the replaceable guide wire 56. A pressure sensing circuit including the resistive sensor elements is completed by connecting the remaining two terminals of the resistive sensor elements to the voltage reference line.

In operation, the electrical sensory circuit functions as follows. The polysilicon sensor elements on the pressure sensor 60 are pressure sensitive. In a particular embodiment having a pair of resistive elements, in response to a change in pressure one element increases resistance and a second element decreases resistance. For example, in an embodiment of the present invention each resistive element has a pressure sensitivity (at 100 mmHg 25 degrees Celsius) of 15-35 microOhms per Ohm/mmHg. By applying a steady current through the resistive elements, pressure changes result in changes in resistance that in turn result in voltage changes across the resistive sensor elements.

A common voltage reference, from which voltages across the first and second resistive elements are measured, is established by connecting a first terminal of each of the pair of resistive sensor elements of the sensor 60 to the common reference voltage provided by the signal conditioning device 50. A differential amplifier within signal conditioning device 50, via the excite/sense lines, senses a voltage difference corresponding to the voltages at the second terminal of each resistive sensor element to establish a voltage difference signal. An analog-to-digital converter ("ADC") within the signal conditioning device 50 converts the amplified analog voltage difference signal into a digital value. The digital value is received by the processor and filtered (e.g. finite impulse response filtered, or "FIR" filtered) in a known manner to render a filtered digital pressure value based upon prior calibration of the sensor 60. The filtered digital pressure value is then utilized to drive a digital input to a pair of output digital-to-analog converters ("DACs"). The pair of output DACs render a differential output signal corresponding to an output signal transmitted on the cable 54 to the physiology monitor 52.

The drive current for each of the sensor 60's polysilicon resistive elements is, by way of example, 30 to 90 microA AC (square wave) operating at a frequency of about 630 Hz. The time-varying nature of the square wave signal facilitates AC coupling between amplifier stages in the signal conditioning device. The AC coupling, in turn, reduces DC signal drift effects.

The polysilicon resistive elements, for example, have temperature sensitivities ranging from about 2.0 to 3.6 mOhms per Ohm/degree C. Because the temperature sensitivities of the resistive elements are not guaranteed to be identical, at least one of the two excitation lines carries an independently adjustable current to facilitate temperature compensation of the pressure sensor as well as, perhaps other characterization-based adjustments applied by the signal conditioning device to provide accurate pressure sensor readings. The separate sensor drive currents facilitate compensating for differences in changes to resistance in the sensor elements over the range of operating temperatures of the sensor 60. Temperature compensation is achieved by adjusting the excitation current driven on at least one of the two excitation lines to the pressure sensor such that the change in voltage across the sensor elements is substantially the same (i.e., within an acceptable error limit) throughout the entire range of operating temperatures. The temperature compensation of the polysilicon resistive sensor elements is discussed herein below with reference to FIG. 3.

Having described the composition of the signals carried by the lines connecting the signal conditioning device to the guide wire-mounted pressure sensor 60, it is noted that the above-described line composition for the cable connector 58 is exemplary. The sensor to which the signal conditioning device 50 is attachable and the composition of the lines between the sensor and signal conditioning device 50 vary in accordance with design considerations and functional requirements associated with alternative embodiments of the invention. For example, other physiologic sensors, such as velocity, flow volume, and temperature sensors, may be used in place of pressure sensor 60, in accordance with the present invention. The composition of the signals on the 10-line connection differs in various alternative embodiments of the invention.

Figure 3:
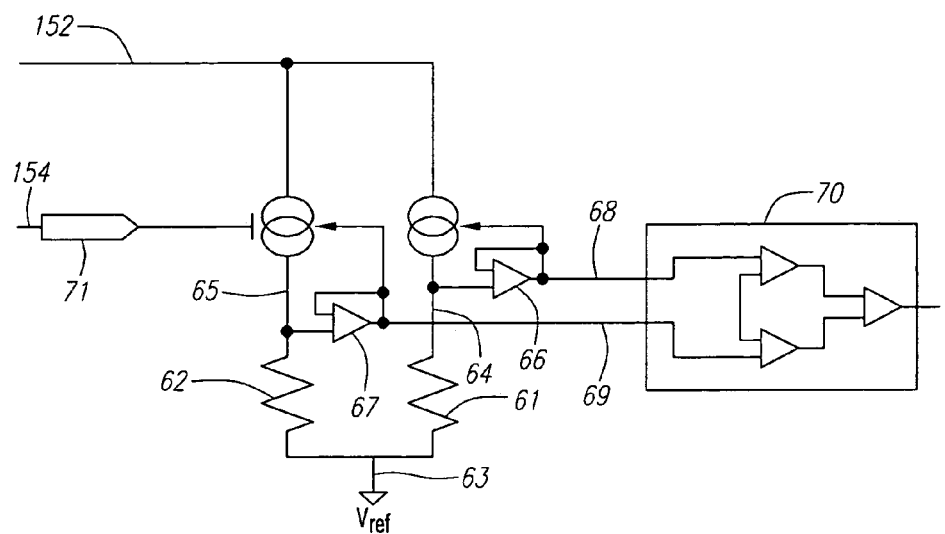
FIG. 3 is a schematic circuit diagram illustrating a portion of the pressure sensor for performing temperature compensation of pressure sensor elements in accordance with an embodiment of the present invention.

Turning now to FIG. 3, a circuit diagram illustratively depicts the sensor/drive circuit of the signal conditioning device 50 and attached guide wire-mounted polysilicon sensor 60. The polysilicon sensor 60 comprises a first resistive polysilicon element 61 and a second resistive polysilicon element 62. The polysilicon elements 61 and 62 share a common reference voltage provided via line 63 from the connector 58. A first excitation current is provided via line 64 to the first polysilicon element 61. A second, adjustable excitation current is provided via line 65 to the second polysilicon element 62. Electrical current passing through each of the two resistive elements 61 and 62 causes a voltage drop across the resistive elements. Since line 63 is connected to both sensor elements 61 and 62, a voltage difference between lines 64 and 65 attached to terminals of the first and second polysilicon sensor elements 61 and 62 is transferred to the output of amplifiers 66 and 67, respectively. A differential amplifier 70 then senses a difference between the output voltages of amplifiers 66 and 67 on lines 68 and 69, respectively.

When a pressure change is applied to the polysilicon sensor 60, the resistance of the first and second polysilicon elements 61 and 62 react in a complimentary manner. In other words, when an applied pressure changes, one of the resistances increases and the other resistance decreases.

The voltage drops across each of the resistive sensor elements according to equation (1):

$$V = I_{(excite)} \times R_{(sensor)} \quad (1)$$

Assuming the excitation current is stable, the voltage change across each of the resistive sensor elements as a result of a change in the resistance of the sensor element follows the equation (2):

$$\Delta V = I_{(excite)} \times \Delta R_{(sensor)} \quad (2)$$

The change in differential voltage (the sum of both voltage changes) between the output terminals 68 and 69 (input to differential amplifier 70) corresponds to the applied pressure.

Ideally, the $\Delta R$ value for each sensor is attributed solely to changes in pressure applied to the sensor. However, temperature changes to the sensor elements also change their resistance. Thus, even in the absence of a pressure change, the resistance (and thus voltage drop) across the two resistive elements 61 and 62 changes in response to temperature changes.

However, differences in voltage change across the sensor elements are of interest rather than the voltage changes across the resistive elements themselves. Thus, if the resistance across the elements 61 and 62 changed exactly the same over the temperature range of interest (or differences were negligible), then temperature compensation is not necessary. However, such matching of resistance change is highly impractical.

The signal conditioning device 50 senses a differential voltage from the sensor elements of the sensor 60. Voltage is the product of resistance times current passing through the resistance. Rather than match resistance changes over a temperature range, in an embodiment of the present invention, temperature-change induced voltage changes across the resistive elements are compensated by adjusting the current through at least one of the resistive elements to compensate for the differences in temperature sensitivity of the two resistive sensor elements. The variation to the current through resistive sensor element 62 is provided by a temperature compensation DAC 71.

With continued reference to FIG. 3, the following equations (3-6) characterize temperature compensation achieved by equalizing the temperature-change-induced voltage changes over a temperature range of interest:

$$\Delta V_a = \Delta V_b \text{(over a temperature range of interest)} \quad (3)$$

Assuming the above Voltage changes are attributed to temperature-induced changes in resistance, then $$(I_a \Delta R_a) = (I_b \Delta R_b); \text{ thus} \quad (4)$$

$$I_b = (I_a \Delta R_a)/\Delta R_b; \text{ and} \quad (5)$$

$$I_b/I_a = \Delta R_a/\Delta R_b \quad (6)$$

For purposes of compensating temperature effects, the resistance changes to the resisters 61 and 62 over the operating temperature range of the pressure sensor are estimated as substantially linear. Thus, by modifying the ratio of the current through each of the elements 61 and 62 in inverse proportion to their resistance changes over the operating temperature range, the changes in voltage across each element 61 and 62 remains substantially equal (within acceptable limits) over a specified compensated operating temperature range. Note that in instances where the temperature effects are not linear (or linear approximation is not acceptable), polynomial compensation equations (based upon temperature) and/or segmentation of the compensated range into sub-ranges can be employed in conjunction with a temperature sensor.

Figure 4:
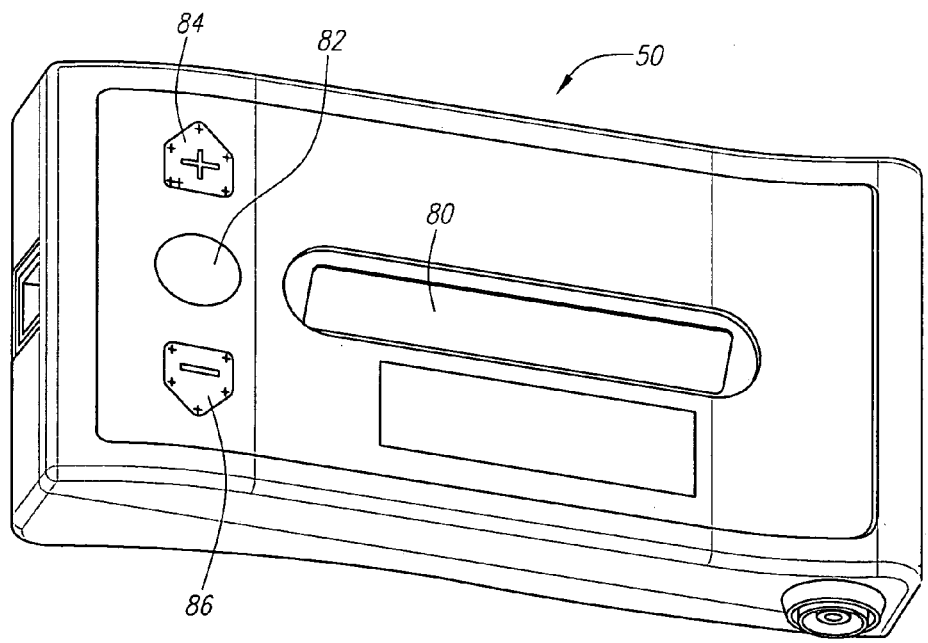
FIG. 4 is an illustrative depiction of a signal conditioning device in exemplary packaging for commercial use.

Turning briefly to FIG. 4, an exemplary physical arrangement user interface for a signal conditioning device 50 is illustratively depicted. The exemplary user interface includes a 120-segment, 8-character alphanumeric LCD display 80. The LCD display communicates various states of the device throughout its operation. The user interface also includes three momentary, normally open switches 82, 84 and 86. The select button 82 enables waking the unit when it has not been used for a period of time and has entered a sleep mode while attached to the physiology monitor 52. The select button 82 facilitates selection of a type of signal represented on the output from the signal conditioning device 50. An exemplary set of output signal modes includes: zero (0 mmHg), 200 mmHg, and Calibration Pulse Sequence (stepping from 0 to 200 Hg in steps of 10 mmHg in half-second time increments). When the signal conditioning device 50 is in an active running mode, the up arrow (+) button 84 allows adjustment of the pressure output in 1 mmHg steps (up to, for example, 30 mmHg). The down arrow (−) button 86 facilitates the complimentary function allowing the output to be adjusted downward.

Figure 5:
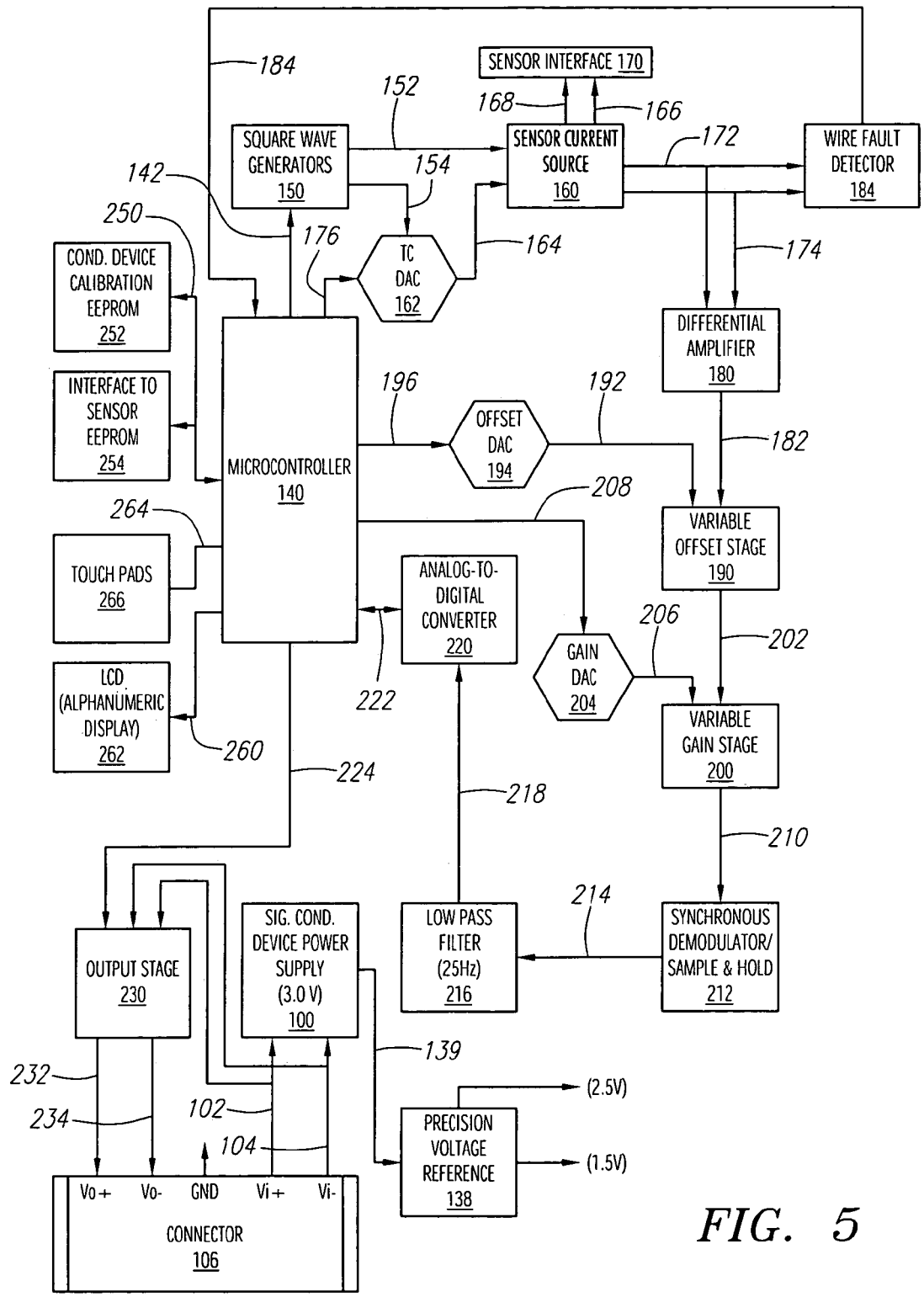
FIG. 5 is a schematic diagram of the primary functional components of an exemplary signal conditioning device.

Attention is now directed to FIG. 5 that schematically depicts the primary functional blocks of the signal conditioning device 50 embodying the present invention. A power supply circuit 100 receives a differential excitation voltage on lines 102 and 104 from a connector 106 that interfaces (via cable 54) to the physiology monitor 52. The power supply circuit 100 converts the differential excitation voltage from a variety of different forms including, by way of example de, sine wave, and square wave AC signals (discussed herein above) to 3 Volts DC. While the typical input is an AC signal, the power supply circuit 100 is also capable of converting a received DC differential input on lines 102 and 104 into the 3 Volts DC power source. The 3 Volts DC supplies the operating power for all circuits within the signal conditioning unit. The power lines to individual functional circuit blocks have been omitted in the drawings to reduce clutter.

Figure 6:
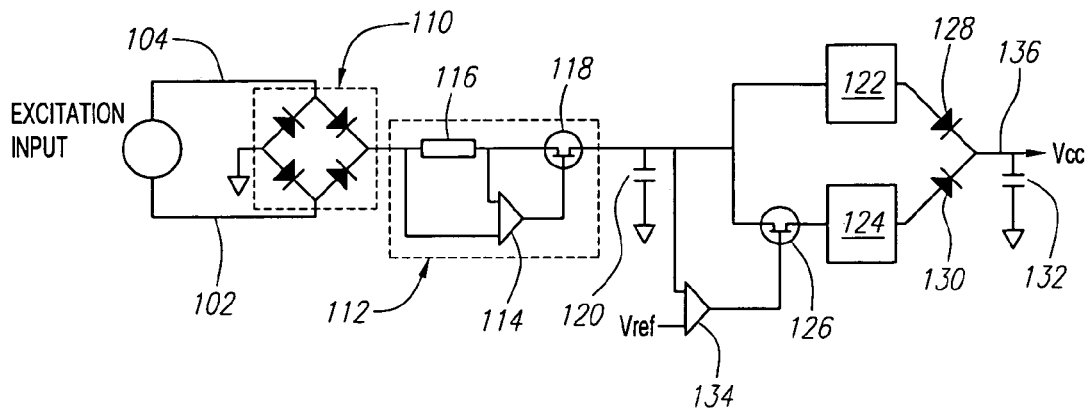
FIG. 6 is a schematic circuit diagram of a power supply circuit incorporated into a signal conditioning device embodying the present invention.

Turning briefly to FIG. 6 that schematically depicts a set of circuits comprising the power supply circuit 100, if the excitation signal on lines 102 and 104 is AC, then the signal is rectified by full wave bridge rectifiers 110, into an unfiltered full wave DC voltage, i.e., without any filter capacitor. A large filter capacitor at the rectifiers would cause excessive surges and waveform distortions due to the capacitive loading—especially on power up. If the excitation signal on lines 102 and 104 is DC, the full wave bridge rectifiers 110 route the most negative terminal to ground and the positive terminal to a following current regulator 112. A differential amplifier 114 monitors the full wave DC current, by the voltage drop across a resister 116. The differential amplifier 114 controls a p-channel field-effect transistor ("PFET") 118 that limits the current to less than 25 mA peak.

A filter capacitor 120 connected to the output of the PFET 118 is charged by the controlled current to nearly the peak of the excitation voltage on the differential input lines 102 and 104. When the filter capacitor 120's voltage is above 3.5 Volts, Vcc is regulated with a low dropout ("LDO") regulator 122 to 3.3 Volts. The current drain in this mode is less than 6 mA. When the filter capacitor 120's voltage is less than the 3 Volts requirement for the LDO regulator 122, a charge pump 124 is energized by a PFET switch 126 to boost the voltage to 3.3 Volts. The current required by the circuit to maintain the 3.3 Volts output (at the inputs to the steering diodes 128 and 130) is higher when in this mode, but it is still less than 15 mA since the Vcc output voltage and power remain constant. The increase in current causes a higher voltage drop across the bridge rectifier 110, slightly lowering the voltage on the filter capacitor 120. This provides hysteresis for the PFET switch 126. A pair of steering diodes 128 and 130 routes the highest voltage output (LDO or charge pump) to the powered circuitry of the signal conditioning device 50. A capacitor 132, attached in parallel to a load, eliminates ripple and crossover spikes from a 3.0 V output power signal on line 136.

A smaller power supply (not shown) provides a bias and Vcc power to operate the current regulating differential amplifier 114. The drop across a full wave rectifier pair supplying power to differential amplifier 114 is much smaller than the pair connected between the input lines 102 and 104 and the current regulator, due to the low current required for the bias circuit. The voltage regulation scheme gives a higher output voltage and will allow proper operation of the power supply circuitry below 2 Volts. A resister limits loading by a filter cap (not shown) that would cause surges and excitation distortion to the bias current to amplifier 114. Part of the filtered, low power Vcc provided as the bias input to the differential amplifier 114 is sent to a 1.234V reference integrated circuit. The 1.234 V reference is divided down to 50 mV by resisters and used to set the current limit in a comparator including the amplifier 114 and the PFET 118. The 1.234 Voltage also sets a trip point for the crossover from a high excitation to a low excitation voltage at a differential amplifier 134 (low voltage switch). When the voltage set by a divider circuit comprising a pair of resisters equals the 1.234 V reference, differential amplifier 134's output switches and turns PFET 126 either on or off.

The 3.0 V output of the circuit illustratively depicted in FIG. 6 is utilized to generate two precision voltages. Returning to FIG. 5 a precision voltage reference 138 receives the 3.0 V reference from the power supply 100 via line 139 and establishes two precision voltage output signals. First, a 2.5 V precision reference output signal is generated by an integrated circuit from the 3.0 Volt output. The 2.5 V precision reference is used wherever high accuracy is required. Second, a 1.5 V reference output signal is derived from the 2.5 V reference via a precision voltage divider. The 1.5 V reference is used to center amplifiers' operating voltage range throughout the signal conditioning device 50 and as the return path (Vref) for the pressure sensor resistors.

With continued reference to FIG. 5, a microcontroller 140, such as microcontroller MSP430P337A, marketed by Texas Instruments of Dallas, Tex., is powered by the 3.0 V power signal output on line 136 of the power supply 100. The microcontroller 140 operates off a 32,768 Hz watch crystal that is multiplied up internally to over 1 MHz. The microcontroller 140 supplies timing and data signals driving the circuitry depicted in FIG. 5. The microcontroller 140 also receives filtered digital signals corresponding to a sensed pressure, and processes the received pressure values (e.g., performs FIR filtering). The microcontroller 140's output and input signals are discussed with reference to the functional blocks depicted in FIG. 5.

Square wave signals, supplied via line 152 to a sensor current source 160 and via line 154 to a temperature compensation DAC 162, are accurately regulated. Such precision is desired because the current across the sensors that measurer pressure is proportional to the supplied signal, and any inaccuracies in the excitation signal on line 152 to the sensor current source 160, or on line 154 to a temperature compensation DAC 162, will affect the accuracy of the signal conditioning device. Thus, in an embodiment of the invention, a pair of precision square wave generators 150 are driven by a timing signal on line 142 from the microcontroller 140. The 2.5 V output of precision voltage reference 138 provides a precision power signal to the square wave generators 15, enabling the square wave generators 150 to supply precision 627 Hz square wave signals to the sensor current source 160 and the temperature compensation DAC 162.

The 627 Hz square wave received by the square wave generators 150 from the microcontroller 140 is approximately 3V. The desired voltage level to the sensor current source 160 is 0.600 Volts peak (1.200 Vp-p), and centered with a DC offset of 1.5 Volts to keep operational amplifiers within the sensor current source 160 within a linear operating range. VMOS FETs within the squarer wave generators 150 precisely regulate the square wave signals having the above-described characteristics provided to the sensor current source 160 and the temperature compensation DAC 162. The VMOS FETs saturate, when the gates are driven high by the 3 V signal from the microcontroller 140. This essentially places the drains at 0 Volts, due to the low 'on' resistance of the FETs and the high value of a pull-up resister attached to each FET's drain. As mentioned above, the 2.500 V precision reference signal from precision voltage reference 138 supplies power to the FETs. With regard to the FET driving the square wave input signal to the sensor current source 160, when the FET is off, a precision resistor divider sets the "high" level of the square wave input. The output voltage on line 152 is 2.106 V. When the FET is on, the output voltage on line 152 drops to 0.904 V. Thus, the peak-to-peak voltage of the square wave on line 152 is 1.202 V, and the square wave signal on line 152 is centered at 1.5 V.

A similar square wave generator, for line 154 to the temperature compensation ("TC") DAC 162, develops a square wave with a 1.200 V peak to peak magnitude. All the DACs within the exemplary circuit (e.g., Texas Instruments' T15616 12-bit DACs), including the TC DAC 162, have an internal gain of two. Therefore the DC offset of the signal driven on line 154 is half of the desired output DC offset of 1.5 Volts, or 0.750 V. The square wave high and low voltages (high/low) are therefore 1.350 Volts and 0.150 Volts, respectively.

The sensor current source 160 receives the square wave input signal on line 152, and a temperature compensation square wave input on line 164 from the temperature compensation DAC 162. The sensor current source 160 provides a first and second excitation current on lines 166 and 168 to a sensor interface 170. The sensor interface 170 passes the signals received on lines 166 and 168 to the resistive sensor elements 61 and 62 on the sensor 60 (see FIG. 3). The sensor interface 170 also provides a 1.5 V precision voltage reference to the sensor 60 to complete the sensor circuit paths through the resistive sensor elements 61 and 62. Sensor output signals on lines 172 and 174 provide a differential voltage signal corresponding to changes in pressure applied to the pressure sensor 60. As discussed previously herein above, the change in differential voltage arises from changes in resistance of the resistive sensor elements 61 and 62 due to applied pressure changes.

Line 166 (corresponding to line 64 in FIG. 3) comprises a fixed current source providing a 60 microamp (peak) current to the resistive sensor element 61. The current on line 166 is proportional to the input voltage (as shown above, 0.600 Vpeak). The peak 0.600 input voltage is developed across the 10K current setting resistor. This sets the current to (0.600/10K) 60 uA peak.

Liner 168 (corresponding to line 65 in FIG. 3) comprises a variable current source providing between 30 and 90 microAmps current to the resistive sensor element 62. The variable current source sums a fixed 1.2 Vp-p square wave arising from the square wave signal on line 152 with a variable square wave from the TC DAC 162 based upon a programmable digital input value transmitted on data lines (not shown) in conjunction with a load signal on line 176 from the microcontroller 140. This summation is developed across a 10K current setting resistor. The current is varied by the TC DAC 162 between 30 uA (peak) with the DAC 162 programmed by the microcontroller with a value of zero and 90 uA (peak) when the DAC 162 is loaded with a full output digital input value (e.g., OFFF).

Amplifiers (see amplifiers 66 and 67 in FIG. 3) buffer the sensed voltages on lines 166 and 168 (lines 68 and 69 in FIG. 3). Pull-up resistors are also attached to lines 166 and 168 to ensure proper detection when the sensor 60 is removed. The pull-up resisters are very large resistances to reduce accuracy errors when the wire is present (e.g., 10 M ohm in parallel with the about 3.5K sensor is 0.04% error).

The buffered sensed voltages on lines 166 and 168 are transmitted as a differential voltage pair on lines 172 and 174 to the input terminals of a differential amplifier circuit 180. The differential amplifier circuit 180 is, by way of example, a small signal amplifier with a gain of 25 and provides good common mode rejection. Feedback resisters and capacitors are included in a known manner to provide stability and reduce the response of the differential amplifier 180 output on line 182 to small phase delays of the wire.

The differential sensor output voltage of the sensor current source 160 on lines 172 and 174 is also passed to a fault detection circuit 184. Each sensor circuit resistance range is 2500 to 5000 ohms. With a 60 uA current through the sensor element 61 and a 30 to 90 uA current applied to sensor element 62, the minimum and maximum voltages across the resistive elements are as follows:

For resistive sensor element 61:

$V(min)=60$ uA*$R$min=150 mV $V(max)=60$ uA*$R$max=300 mV

For resistive sensor element 62:

$Vb(min)=30$ uA*$R$min=75 mV $Vb(max)=90$ uA*$R$max=450 mV

A window detector circuit within the fault detection circuit 184 monitors the minimum and, maximum sensor square wave voltage. The voltage is compared to set limits defined by a resistor divider network. For a fault condition, Rmin and Rmax limits were set to values that are guaranteed to be abnormal (e.g., 8.7 K ohms and 1.5 K ohms) and corresponding maximum and minimum voltages (e.g., 2.02 V and 1.55 V). The voltage limits set the range of the window comparator. When the input voltage is beyond the range of the window, the output of the comparators switch. The four comparators are fed to the microprocessor and indicate a fault. The outputs of the comparators have long time delays to prevent momentary glitches from causing nuisance faults. The fault detection circuit provides three fault status signals on lines 186 to the microcontroller 140. Two lines identify a short for each of the two resistive sensor elements 61 and 62 on the sensor 60. A third line identifies an instance where the guide wire 56 is not attached to the signal conditioning device 50.

A next stage of the signal conditioning device 50, a variable offset stage 190, receives an amplified differential output signal on line 182 from the differential amplifier 180. The variable offset stage 190 also receives an offset voltage signal via line 192 from an offset DAC 194 (programmed by a value transmitted on data lines in conjunction with load select line 196 from the microcontroller 140). The variable offset stage 190 facilitates nulling an offset due to an imbalance arising from temperature compensation performed by the TC DAC 162. After compensating the resistive sensor elements 61 and 62 for temperature, the current passing through each of the elements 61 and 62 in most instances are not equal. As a consequence, a differential voltage is present between the signals transmitted on lines 172 and 174 when there is there is no applied pressure. An offset voltage supplied by the offset DAC 194 via line 192 nulls the voltage difference so that an input to an analog to digital converter 220 is set to a voltage representing 0 mmHg (approx. 729 mV). The acceptable window for 0 mmHg that the microcontroller 140 can accommodate is 0.5 to 1.0 Volts. The microcontroller 140 internally corrects voltages within this window. The offset value is affected by the gain of a variable gain stage 200. The microcontroller 140 takes the gain stage into account when setting the offset DAC 194. In an embodiment of the signal conditioning device, the offset stage 190 also has a fixed gain of five to reduce the gain that would otherwise be required by the differential amplifier 180—which would reduce the differential amplifier 180's bandwidth.

The offset required is dependent on the sensor specification's worst case study. In an embodiment of the signal conditioning device, a maximum offset from the sensor is 33 mV. After the differential amplifier gain of 25, the offset has increased to 825 mV. Taking variations in atmospheric pressure and pressure measurements into account, the offset range is, for example, increased to 1.0 Volts for margin.

An output signal on line 202 from the variable offset stage 190 is received by the variable gain stage 200. The variable gain stage 200 applies a variable gain, determined by input from a gain DAC 204 via line 206. The gain DAC 204 receives a programmed gain value (a calibration value supplied by the sensor 60's EEPROM) in conjunction with a selection signal transmitted on line 208 from the microcontroller 140.

In an exemplary embodiment of the signal conditioning device 50, the total system gain (based on the sensor specifications) is 125 to 2500. Therefore, taking into consideration the gain of the previous two amplifier stages (i.e. 25 and 5) the last stage must have, a gain between 1 and 20. The microcontroller 140 obtains the gain for a connected sensor by reading the sensor 60's EEPROM and transmits a corresponding value via data lines (not shown) to the selectable gain DAC 204's data input. The output of the variable gain stage 200 is transmitted on line 210.

A synchronous demodulator circuit 212 extracts voltage peaks from a square wave signal arising from the square wave input to the sensor and signal conditioning circuits that act upon the sensed pressure signal. In an embodiment of the invention, rather than operating a DC coupled system that is prone to drift and high cumulative offsets, an AC system was created to block DC signal components. Square waves were adopted in the illustrative embodiment since the levels are more easily measured on an oscilloscope and aren't prone to phase errors associated with sine waves when voltage are summed. In an illustrative embodiment of the present invention, the peak level of the square wave input via line 210, an AC coupled waveform, is demodulated by the synchronous demodulator circuit 212 to render a DC level signal.

Figure 7:
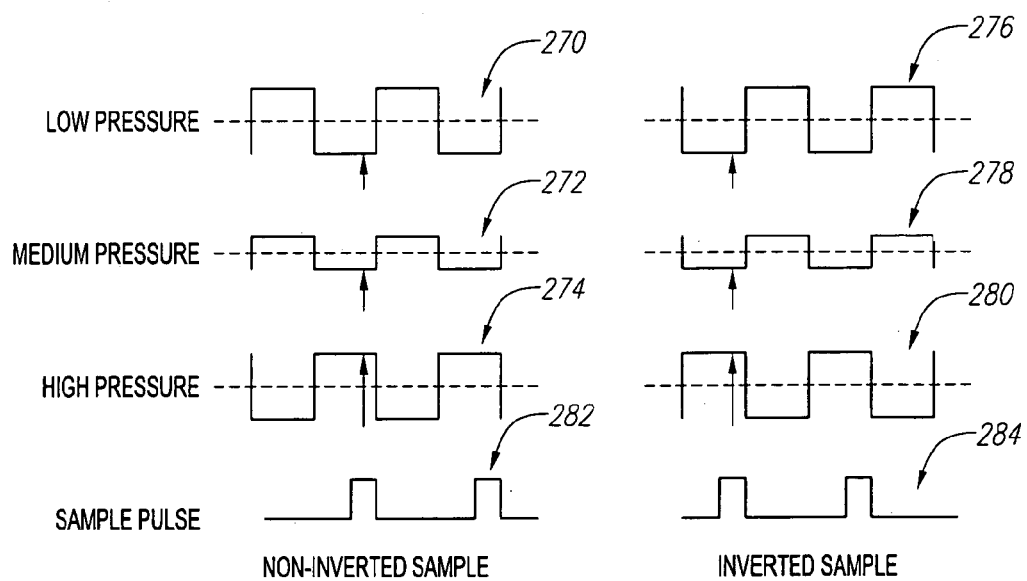
FIG. 7 is a waveform diagram illustratively depicting a demodulation scheme for extracting peak voltages from an output waveform of analog signal conditioning components of the signal conditioning device.

Demodulation is achieved by synchronously sampling the last 50% of each peak (positive and negative) of the square wave (see FIG. 7). Under the control of a timing signal from the microcontroller 140, the synchronous demodulator circuit 212 samples both the halves of a full square wave cycle by inverting the square wave and sampling, in addition to the non-inverted half peak (depicted as signal waveforms 270, 272 and 274 on the left side of FIG. 7) a half peak of the inverted signal (depicted in waveforms 276, 278 and 280 the right side of FIG. 7). The sample pulses (active high) are depicted in as waveforms 282 and 284 for the non-inverted and inverted waveforms, respectively.

Figure 8:
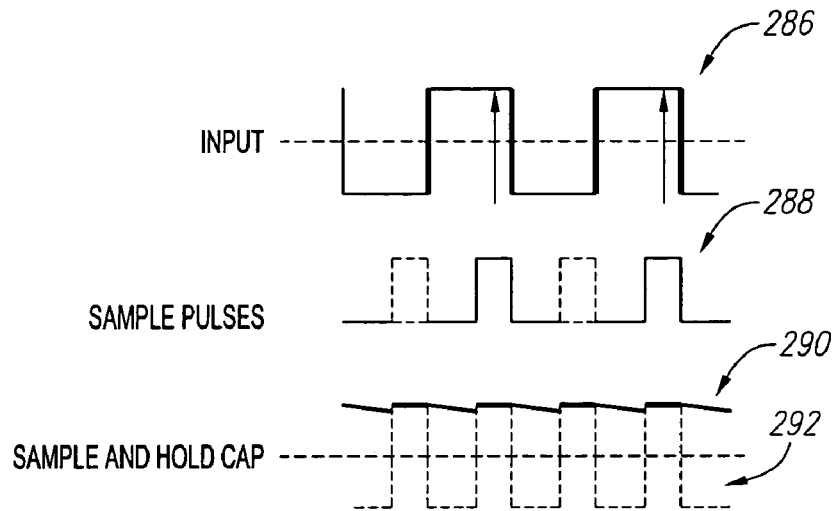
FIG. 8 is a waveform diagram illustratively depicting another aspect of the demodulation scheme enabling signal sampling at a rate that is twice the input waveform repetition rate.

The positive and negative peak voltages are stored on a sample-and-hold capacitor in the synchronous demodulator circuit 212. The charge stored upon the capacitor renders a DC voltage corresponding to the peak value of the square wave. The capacitor stores the acquired charge between samples (by the ADC 220), though a small discharge of the capacitor during the non-sample period causes ripple. With reference to FIG. 8, the inverted sampling scheme allows two samples to be taken from input waveform 286 each period, in accordance with the sample waveform 288 (inverted sample is shown as a ghost outline)—thereby providing better accuracy and less ripple in the output signal (depicted as waveform 290 and actual sample input 292—in ghost outline) from the synchronous demodulator circuit 212 on line 214.

A demodulator filter stage 216 is a low pass filter that eliminates the 627 Hz ripple of the sample-and-hold circuit and provides some reduction of 50 and 60 Hz noise. The corner frequency is set in conjunction with the controller 140 firmware's FIR filter to give a system bandwidth of 25 Hz.

A low-pass filtered output on line 218 is received by an analog-to-digital converter 220. The output of the ADC 220 is sampled at a rate of 256 Hz (interrupt driven by the microcontroller 140) through clock, control and data lines 222 linking the ADC 220 to the microcontroller 140. After receiving the filtered, digitized signal from the ADC 220 via lines 222, the microcontroller 140 performs additional operations (e.g., FIR filtering) on the received data, then outputs the value via lines 224 to an output stage 230. The output stage 230, comprising two digital-to-analog converters, receives power from the differential excitation signal on lines 102 and 104 of the cable connector 106 and digital control data (for the DACs) on lines 224. The output stage generates a differential output voltage on lines 232 and 234 to the cable connector 106.

Figure 9:
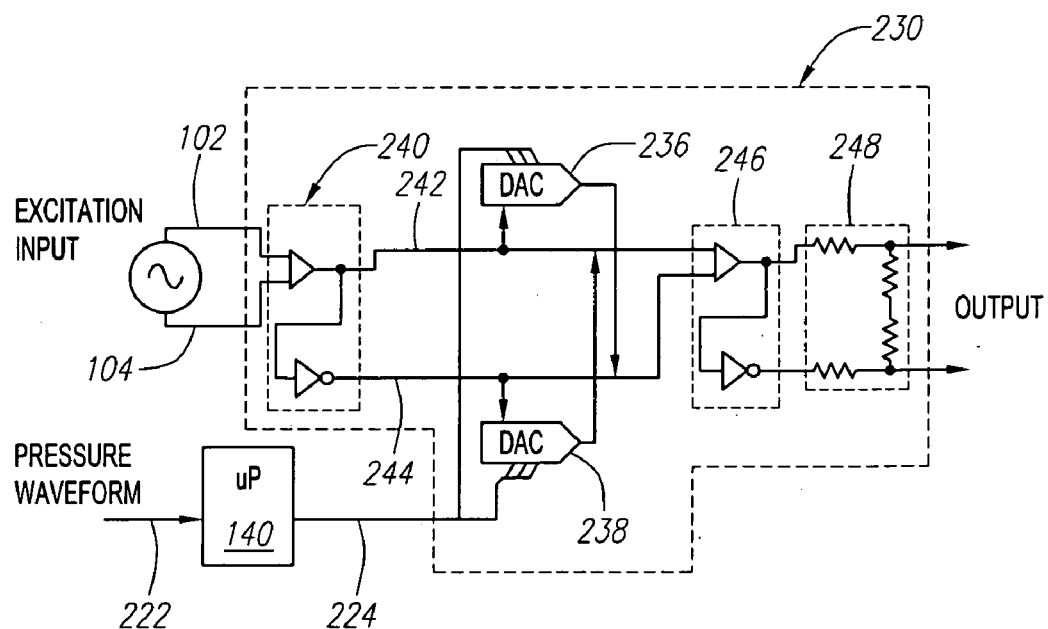
FIG. 9 is a schematic circuit diagram of an output stage providing a differential output from the signal conditioning device to a physiology monitor.

Turning briefly to FIG. 9, the output stage 230 modulates the excitation signal received from the physiology monitor 52 via cable 54, which can be either DC or AC, with a pressure waveform to develop a signal proportional to the excitation signal magnitude and a sensed pressure. The microcontroller 140 receives a digitized pressure waveform input from the ADC 220 via lines 222, applies an FIR filter, applies offset and gain adjustments for the output stage, and sends the digital information via lines 224 to a pair of DACs 236, 238 within the output stage 230.

The digitized pressure waveform values transmitted by the microcontroller 140 to the DACs 236 and 238 modulate the excitation signal (buffered and inverted buffered by buffer stage 240) transmitted via lines 242 and 244 to the output stage 230's DACs 236 and 238 reference inputs. The two DACs 236, 238 generate a differential output that replicates the excitation voltage but are of opposite polarity. The differential signal output from the two DACs 236, 238 subtracts from the differential excitation signal transmitted on lines 242 and 244. Since the signals are differential, DC offsets introduced by the DACs 236, 238 or the excitation signal do not create issues for biasing the output amplifiers into their linear range. Thus, the output stage 230 is DC coupled—a general requirement for instances wherein a DC excitation signal source is utilized.

Additional signal conditioning is applied to the modulated excitation signal on lines 242 and 244 before the differential pressure signal is output on the cable 54. First, the differential signal passes through a buffer/inverted-buffer stage 246. Second, the buffered output of the buffer stage 246 is attenuated by a resister network 248. When the sensed pressure is at 0 mmHg, the DACs 236, 238 null the excitation voltage so the differential output is zero volts across the output attenuator stage 248. The attenuator stage 248 resistance is selected to enable the circuit to satisfy the AAMI requirements for a low output impedance and a differential voltage equal to 5 uV/V/mmHg. The amplifier circuits in the buffer stages 240 and 246 have a bandwidth greater than the maximum excitation frequency. Feedback capacitors on the buffer amplifiers in stages 240 and 246 limit maximum bandwidth (frequency response), while ensuring stability of the output.

The microcontroller 140 interfaces with a number of peripheral components. A set of data/clock lines 250 interface to calibration information. The signal conditioning device 50 includes a calibration EPROM 252, including a set of values entered during manufacturing characterizing the operation of the circuits. The set of values stored in the EPROM 252 during calibration of the signal conditioning device 50 include: calibration data for the input stage (e.g., gain DAC), calibration data for adjusting the gain of the output stage (e.g., output DACs), and data checking (e.g., checksum). The set of data/clock lines 250 are also connected to an external sensor interface 254 that facilitates extracting a set of calibration/characterization data for the resistive sensor elements 61 and 62 on the guide wire-mounted pressure sensor 60. The information stored within the EEPROM includes temperature compensation offset, gain and offset values. The microcontroller 140 reads the EEPROM values once during set up of the TC DAC 162, offset DAC 194 and gain DAC 204. The calibration/characterization data is, for example, stored within an EEPROM attached to a guide wire that carries the sensor 60.

Additional data/control lines support the user interface elements of the signal conditioning device described with reference to FIG. 4. A set of lines 260 supply data/control to an LCD output circuit 262. A second set of lines 264 interface the microcontroller 140 to touch pads 266.

Having described the components and functional blocks of the signal conditioning device 50, attention is now directed to the calibration, setup and operation of a system including the signal conditioning device 50.

Manufacturer Signal Conditioning Device Calibration

The conditioning device 50 includes both an input (patient side) and output (physiology monitor side) that are calibrated during manufacturing. The signal conditioning device 50's sensor input is calibrated during manufacturing test to facilitate greater precision in the display and calibration transfer functions. In particular, after connecting a calibration standard (e.g., a mock sensor providing a differential resistance) to the signal conditioning device 50 and entering an input calibration mode, the signal conditioning device 50 polls the analog differential voltage input. Calibration input voltages are read and checked. Thereafter, the signal conditioning device 50 performs an auto zero function on a differential voltage input corresponding to 0 mmHg. Next, the sensor input of the signal conditioning device 50 is calibrated for a signal input intended to represent 200 mmHg. If the difference between the 200 mmHg reading and the zero reading is greater than 3 percent of the reading (i.e., +−0.6 mmHg at 200 mmHg), then a fatal error is registered. If the difference is within 3 percent (i.e. +−0.6 mmHg), then the difference between the actual value at 200 mmHg and the theoretical value (based upon the zero point) is stored and used to modify the gain DAC code for each wire attached to the signal conditioning device.

Output calibration has two modes of operation: manufacturing test and field adjustment. During manufacturing, the signal conditioning device 50 output to a physiology monitor is calibrated to provide a standard 5 μV per Volt/mmHg output signal. In the manufacturing test mode, a technician adjusts a scale factor up/down to achieve a desired output. The adjustment coefficients established during testing are saved within the signal conditioning device 50's EEPROM. In the field, the output is adjusted to meet the signal input requirements for a particular physiology monitor. After connecting the signal conditioning device 50 to the physiology monitor 52, a user is prompted to press the up/down arrows until the output on the physiology monitor reads 0 mmHg. Once the 0 mmHg output is established, the user is prompted to press the up/down arrows until the output signal is properly scaled such that the physiology monitor reads 200 mmHg.

Guide Wire EEPROM-Based Signal Conditioning Device Calibration

With regard to the guide wire 56 "input" calibration, a guide wire 56 supplies sensor characterization data from its EEPROM upon connection to the signal conditioning device 50. The EEPROM read/write functions are performed via a standard two-wire serial interface (data, or "SDA", and clock, or "SCL") well known to those skilled in the art. Each attached guide wire-mounted sensor contains a piezoresistive pressure sensing element having a particular pressure/temperature response. During manufacturing, the pressure/temperature response is determined and signal conditioning values for yielding consistent output are stored within the EEPROM mounted upon a housing of the guide wire. These values include: a temperature coefficient offset current, signal conditioning gain, position offset default, and checksum. These values are applied to the above-described signal conditioning DACs to modify a sensor current and a differential voltage representing a sensed pressure.

After reading the characterization data from the EEPROM, the signal conditioning device 50 applies the provided calibration information to its conditioning circuitry. The calibration information includes a temperature compensation value applied to the temperature compensation DAC 69 that modifies input current to the compensated resistive sensor element 62. As discussed herein above with reference to FIG. 3, modifications to the current through resistive sensor "$R_b$" 62 substantially reduce, if not effectively eliminate, the effect of temperature upon the differential signal read from lines 68 and 69 over a specified operating temperature range. The calibration information also includes gain and offset values applied to gain and offset DACs that modify an analog differential voltage derived from lines 68 and 69. The temperature compensation and gain coefficients are fixed at the time of manufacturer testing. The offset coefficient is a default value that is modifiable once loaded during start up.

After applying the calibration information to the conditioning circuitry, based upon the guide wire sensor EEPROM-supplied calibration data, the signal conditioning device 50 transmits a square wave excitation pulse to the AC coupled sensor 60 and reads differential voltage signals via the sensor interface. The excitation pulse is a square wave driven by a timer output of the microcontroller at approximately 630 Hz. Demodulation pulses are driven at the same frequency as the excitation pulse, but have differing duty cycles. The sensor voltage is measured to ensure a signal within an expected range. Detected errors include "no wire" and "shorted wire" present.

User Calibration of the Signal Conditioning Device

After the signal conditioning device 50 applies the contents of the guide wire-mounted EEPROM to its DACs and confirms that the sensor 60 is properly connected, the signal conditioning device 50 tests its output via cable 54 to the physiology monitor 52. The output from the signal conditioning device 50 to the physiology monitor 52 pulses from 0 to 200 mmHg in 10 mmHg increments every half second to enable an operator to verify the offset and gain via the output of the physiology monitor 52.

With regard to the connected guide wire 56 and connector cable 54, the signal conditioning device 50 performs an auto zero operation. Auto zeroing establishes the currently sensed pressure as the zero, or reference, pressure. The output of the signal conditioning device on the cable 54 to the physiology monitor 52 is a voltage corresponding to the 0 mmHg level. Thereafter, in response to disconnecting and reconnecting the guide wire 56, the signal conditioning device will initiate re-zeroing the output.

The auto zero routine, executed in response to initially sensing a guide wire attached to the signal conditioning device 50, comprises two main stages. During a first stage of the auto zero routine, the microcontroller determines whether an amplifier stage has "railed". The analog-to-digital mapping in the signal conditioning device is from −210 mmHg (zero counts) to 510 mmHg ($FFF counts). The full scale range is only a portion of this region (e.g., −30 to 330 mmHg). One potential cause for "railing" is utilizing the sensor apparatus at an altitude that significantly differs from the altitude of the initial sensor calibration location. If the amplifier has railed, then the microcontroller attempts to bring it back into its linear gain region. Therefore, during the first stage, the amplifier is de-railed by sampling the sensor over a half-second period, averaging the samples, and then calculating steps ("counts") in the offset DAC needed to place the "zero" reading within 50 mmHg of a preferred zero point (e.g., $4AA). The count value is repeatedly adjusted until the target region is reached.

After the amplifier is derailed, during the second phase final adjustments are made to establish a zero input reading. The microcontroller also checks for a varying input signal symptomatic of a guide wire sensor being placed prematurely within a body. During the second phase, sampling takes place over a four-second period. During zeroing, the gain DAC 204 code is read and the microcontroller computes an adjustment transfer function according to the equation (7):

$$\text{Steps} = \Delta\text{ADC counts} * (\text{Volts}/\text{ADCcounts}) * (\text{Steps}/\text{Volt}) * 1/\text{Config.Gain} \quad (7)$$

Where

Config.Gain=Base of Variable Gain+(Gain DAC code*Gain/DAC code.

For example, if the gain span is 5 to 100 using a 12 bit DAC the Gain/DAC code=95/4096, and a DAC Code of $1A5 (421) yields:

Config.Gain=5+(421*95/4096)=15 (approximately).

1/Gain=$8000/(Configured Gain in Hex) *Note: this is a Q15 (i.e. a binary fractional value with a sign bit and 15 bits of resolution) number.

Steps/volt=1/(2*Ref Volt*(offset circuit gain)*1/4096.

Volts/ADC count=Ref_Volt/4096.

Where: Volts/(ADC counts)=2.5/4096.

Converting to Q15 renders a value of $0014.

Zero Point-Zero Measured=$\Delta$ADC counts, and Number of Steps (+/−)=$\Delta$ADC counts/ADC counts per step. The calculated number of steps is compared to a current offset to determine whether the adjustment is possible (i.e. a value of minus 10 if the DAC is current at 8 would render a negative (erroneous) value for the DAC).

After auto zeroing, the signal conditioning device 50 output to the physiology monitor via cable 54 is adjusted using the up/down (.+−.) arrow buttons 84 and 86. The adjustment, referred to as "normalization", modifies an internal offset (normalization) variable within the microcontroller. The internal offset variable is added to the computed output pressure sample prior to sending an output sample value to the output DAC. The up/down adjustment is typically performed after the pressure sensing guide wire 56 is inserted within the body (e.g., near an aortic pressure sensor).

Running Mode

In a run mode, the signal conditioning device 50 receives a differential analog voltage signal indicative of applied pressure changes to the sensor 60 and computes and outputs a corresponding pressure signal on the cable 54 to the physiology monitor 52. The LCD 80 reads "RUNNING". The sample and update rates for the signal conditioning device 50 are sufficiently high to accommodate blood pressure change rates and sufficiently low to ensure that sufficient power exists for the microcontroller to operate. An exemplary sampling rate is approximately every 4 milliseconds. However, a wide range of sampling rates will be deemed satisfactory to those skilled in the art when taking into consideration the above-cited factors.

The microcontroller applies FIR filtering to the sampled data to improve signal quality. In the exemplary embodiment, the Texas Instruments MSP430P337A microcontroller includes a built-in signed multiply, accumulate peripheral allowing fast multiplication. FIR coefficients are stored in on-device read-only memory ("ROM"). The number of coefficients is determined by the factors of the response requirements and the time for executing the filter function on a microcontroller running at a relatively slow clock cycle to reduce power consumption.

The microcontroller 140 scales the output prior to sending values to the output DACs 236, 238. The mapping of input values from the ADC converter 220 applies to the output DACs 236, 238. The output zero is absolute while the input zero from the ADC converter 220 is allowed to float between .+−.100 mmHg around an ideal zero point. During zeroing the signal conditioning device establishes the amplifier operating range (via the offset DAC) and performs an average on the received zero input signal. The averaged value is used as a reference for subsequent measurements (the reference is subtracted from the readings during the running mode). This value is then multiplied by the output attenuation coefficients prior to transmission to the DACs 236, 238.

The LCD 80 of the signal conditioning device 50 is capable of displaying the maximum and minimum pressure over a most recently completed sample interval (e.g., 4 seconds). The microcontroller converts the digital output value (counts) to mmHg (binary) and then converts the binary mmHg value in a known manner to binary coded decimal digits (hundreds, tens and ones). The digits are converted to segments in the LCD display and then latched to turn on appropriate LCD 80 segments.

Figure 10:
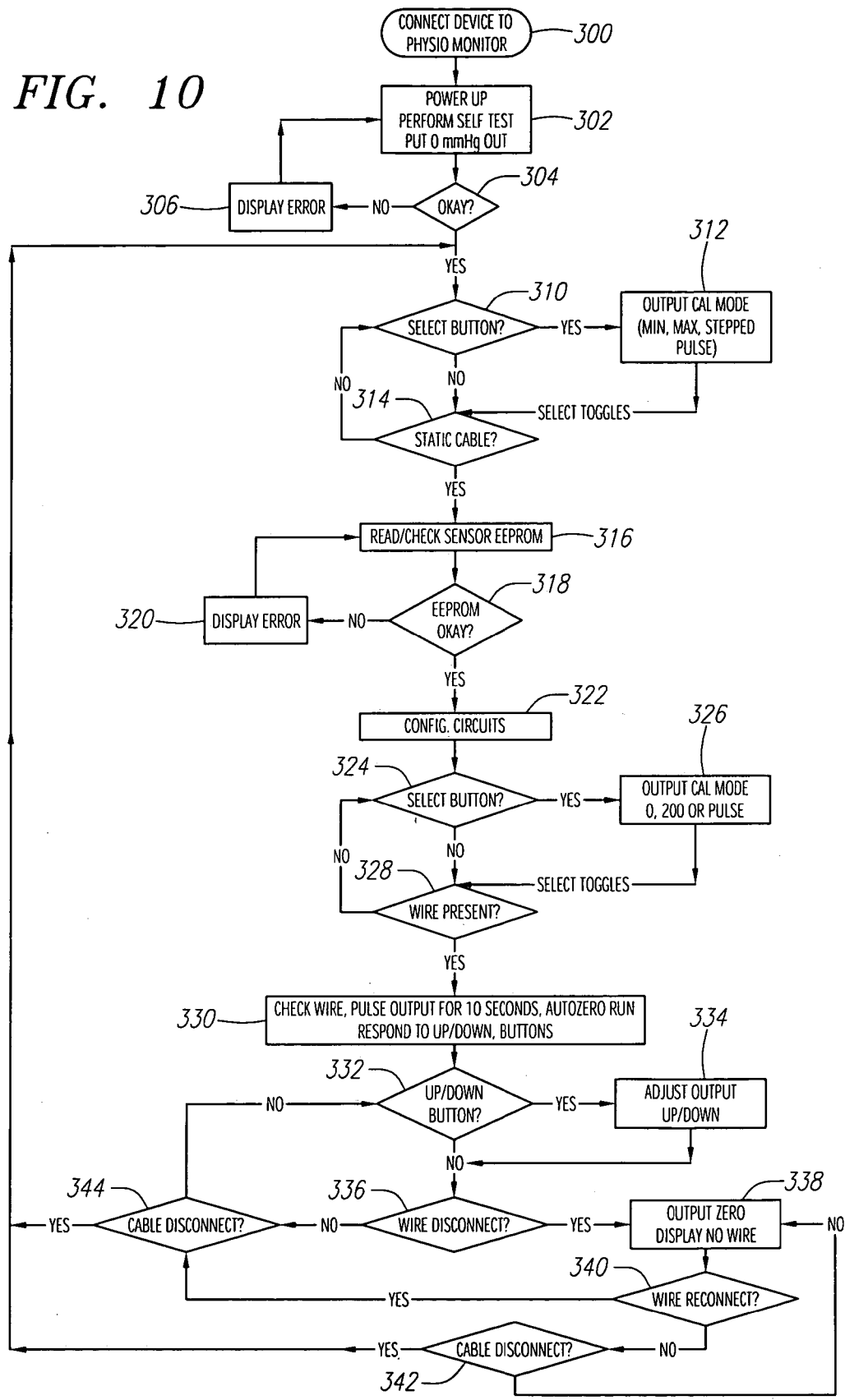
FIG. 10 is a flowchart summarizing the operation of an exemplary signal conditioning device embodying the present invention.

With reference now to FIG. 10, a flowchart summarizes a set of functional operations performed by the signal conditioning device 50. Initially, during step 300 the signal conditioning device 50 is connected to the physiology monitor 52 via the cable 54. In response to power supplied by the physiology monitor 52 via the excitation signals carried by the cable 54, during step 302 the signal conditioning device 50 performs power-on self testing and output a value of 0 mmHg to the physiology monitor. If during step 304, the device 50 detects an operation error, then control passes to step 306 wherein an error message is displayed on the LCD output of the signal conditioning device 50. Control passes back to the self-test step 302.

If however, the self-test is successful, then control passes to a state wherein the signal conditioning device 50 checks for connection of a guide wire cable connector 58 (indicating that a guide wire has been attached), and enters a mode wherein it responds to selection of the interface buttons 82, 84 and 86. During step 310, if a calibration sequence is selected using the interface buttons, then control passes to step 312 where the user is prompted to adjust the output signal. Modes of output calibration include 0 mmHg, 200 mmHg and pulse calibration mode wherein the output to the physiology monitor alternates between 0 mmHg and 200 mmHg for a period of time. A user enters a button selection input to exit the calibration mode and pass to step 314.

At step 314 the signal conditioning device determines whether the sensor static cable (containing the characterization EEPROM) is attached to the signal conditioning device 50 (step 314 is also entered from step 310 if the calibration button selection was not sensed). If the signal conditioning device 50 does not sense an attached static cable 59, then the LCD display reads "no cable" and control passes back to step 310.

If the signal conditioning device 50 does sense an attached cable, then control passes to a step 316 wherein the signal conditioning device reads the content of the characterization EEPROM describing the operating characteristics of the sensor carried by the attached guide wire. During step 318, if the EEPROM values are invalid (e.g., a checksum error), then an error message is displayed during step 320 and control returns to step 316. However, if the values are valid, then the values are used to configure the circuitry of the signal conditioning device 50 during step 322. Thereafter, during step 324 if the signal conditioning device determines that the user has entered a calibration mode button selection sequence, then control passes to step 326, wherein steps are performed for calibrating the endpoints and intermediate steps within the range out output for the signal conditioning device. This mode is exited by a predetermined button selection sequence entered by the user, and control passes to step 328 (also entered when the calibration button sequence is not sensed during step 324).

It is possible for the static cable 59 to be attached, while the guide wire 56 is detached. Thus, during step 328 if the guide wire 56 is not attached, then control returns to step 324 (and "no wire") is displayed upon the signal conditioning device LCD output. Otherwise, if the wire is attached, then control passes to step 330 wherein the signal conditioning device enters a run mode wherein it checks the sensor wire, pulses an output between zero and 200 mmHG for 10 seconds, performs autozero on the sensor input, and senses input values and generates output values to the physiology monitor.

The signal conditioning device also responds to inputs from the select, "+" and buttons and responds accordingly. The select button causes the signal conditioning device 50 to output a currently calculated sensed pressure (the calculated maximum and minimum pressures over the last two seconds) on the LCD screen. Otherwise the LCD merely outputs "running" and provides a differential output signal to the physiology monitor via cable 54.

During step 332 if either of the up/down buttons have been pressed, then control passes to step 334 wherein the output is adjusted either up or down according to the pressed button. If, during step 332, the up/down buttons have not been pressed, then control passes to step 336. During step 336 if a sensor wire disconnect is sensed, then control passes to step 338 wherein the signal conditioning device 50 outputs an output on cable 54 representing zero, output and the LCD displays "no wire." Control then passes to step 340.

At step 340, if a wire re-connect is not sensed, then control passes to step 342. If during step 342, the static cable is not disconnected, then control returns to step 338. Otherwise, if a cable disconnect is detected, then control returns to step 310. If, at step 340 a wire reconnect is sensed, then control passes to step 344. During step 344 if a cable disconnect is sensed, then control passes to step 310. Otherwise, if the static cable is still connected, then control returns to step 332.

Having described an exemplary set of steps (stages or states) associated with the operation of a signal conditioning device 50 embodying the present invention, it is noted that in alternative embodiments, the steps are modified to include additional functions, remove functions, and re-arrange the sequence of operations performed by the device. Such modifications are contemplated in view of the flexibility of programming such a device in a manner well known to those skilled in the art.

Figure 11:
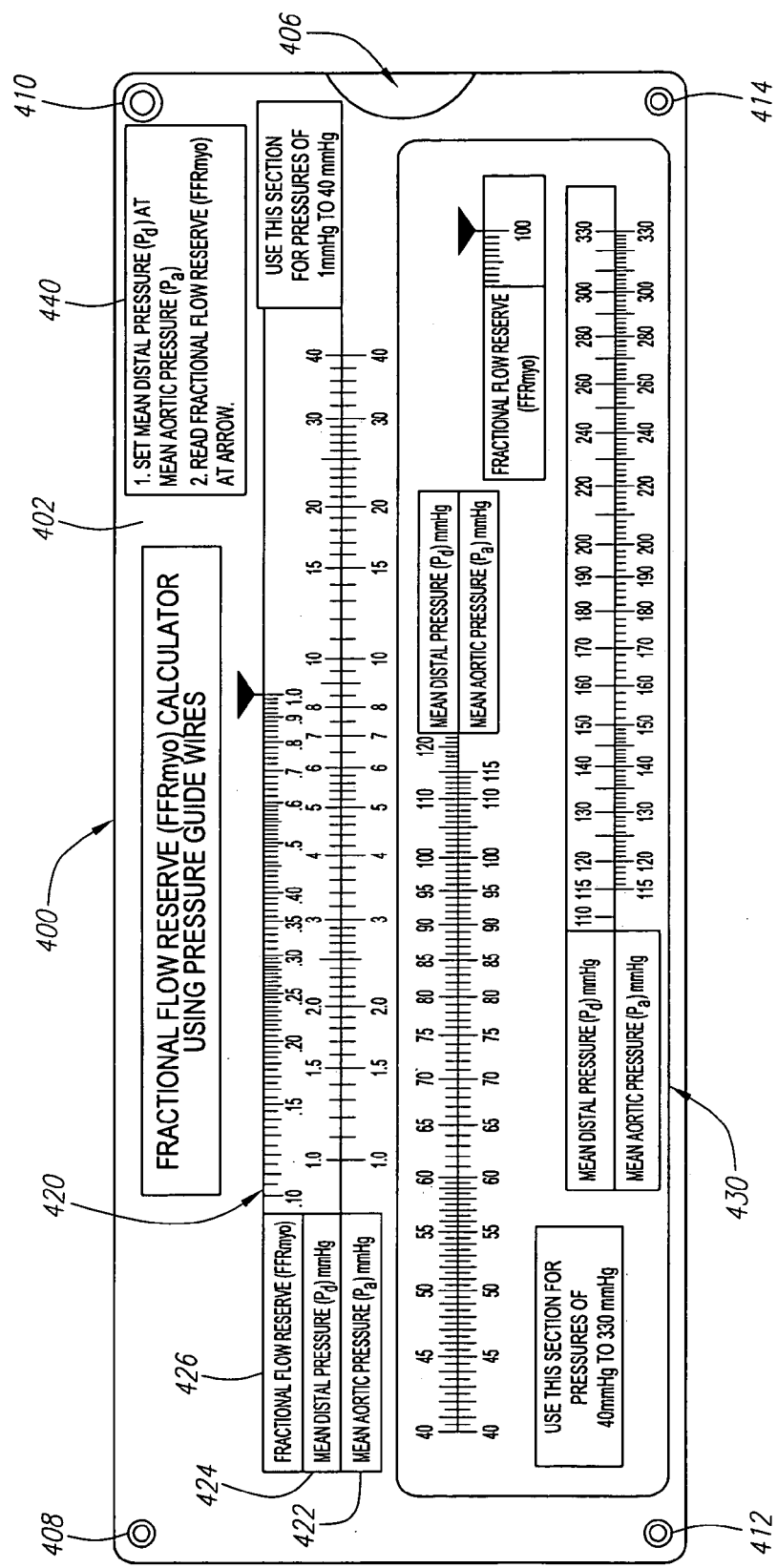
FIG. 11 illustratively depicts a front view of a slide rule device utilized to compute a blood flow restriction measure, known as fractional flow reserve.
Figure 12:
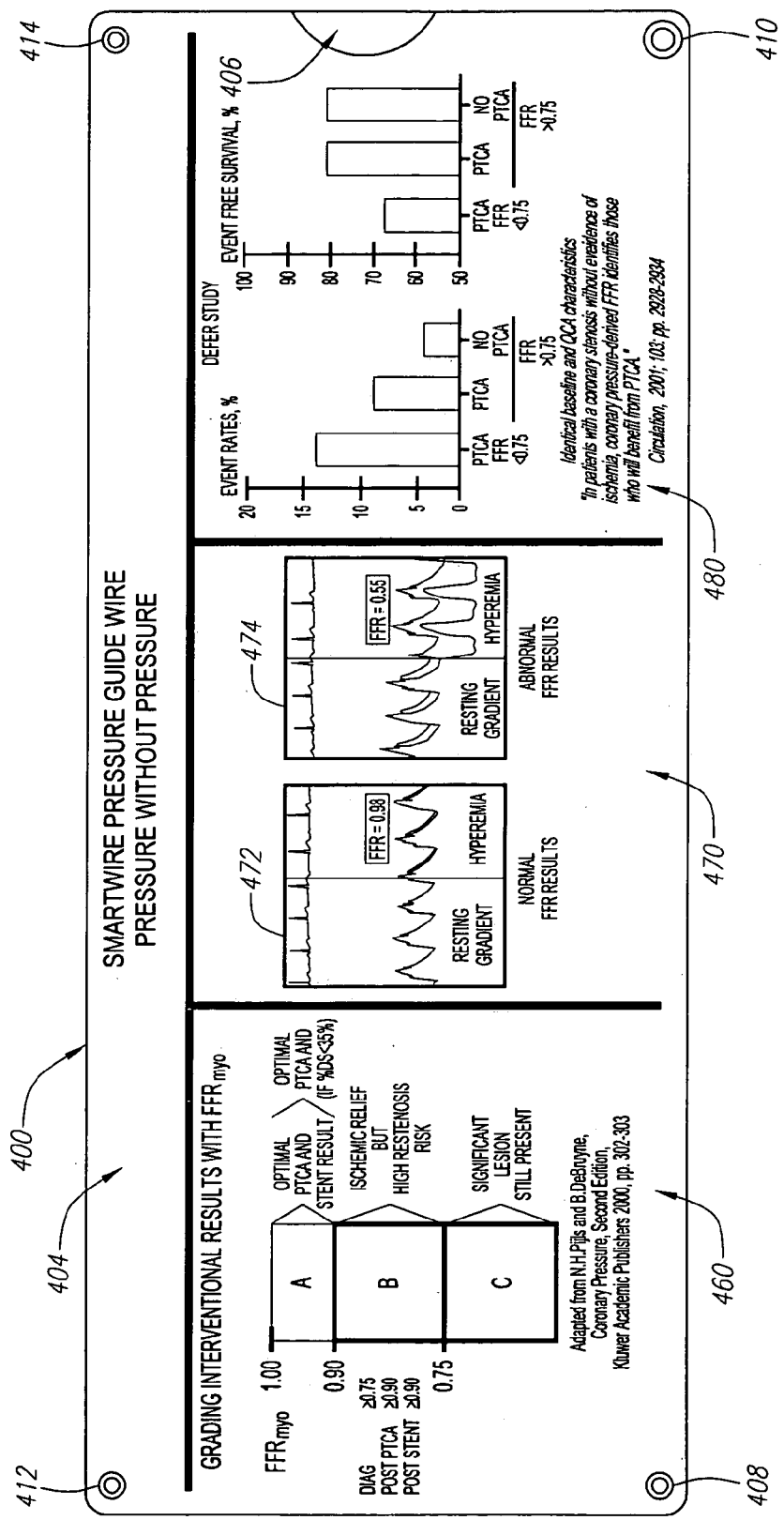
FIG. 12 illustratively depicts a back view of the slide rule device.

Another aspect to the exemplary system incorporating the present invention is its use to treat patients in a medical establishment. Part of such treatment involves the determination of the severity of a vessel blockage and determination of a course of treatment. With reference to FIGS. 11 and 12, a front and back side, and sliding insert of a slide-rule type device 400 are depicted. The slide-rule type device is utilized in conjunction with pressure readings provided by the signal conditioned guide wire-mounted pressure sensing system to render a fractional flow reserve value. The fractional flow reserve value calculated on the front side of the slide-rule type device 400 depicted in FIG. 10 is then utilized to render treatment guidance in accordance with the charts depicted on the back side of the device 400 that is depicted in FIG. 12.

Referring first to FIG. 11, fractional flow reserve ("FFR") represents a degree of occlusion in a blood vessel arising from a stenosis as represented by pressure measurements from within a blood vessel. FFR is calculated as a ratio of two pressure sensor readings within an artery. The first value represents a sensed pressure taken at a side of a blood vessel from which blood flows toward a stenosis. This is the higher of the two pressure readings. The second pressure value, by which the first value is divided, is taken at the opposing side of the stenosis. The slide-rule device performs the division by matching the first and second values at the designated portions of the slide rule scales. The FFR valuer is then read from the corresponding result scale. The slide-rule device depicted in FIGS. 11 and 12 is constructed in three parts: a front face plate 402, a back face plate 404, and a sliding insert 406 (viewable through a pull tab 405 cut in the front face plate 402). The front and back face plates 402 and 406 are bound together, for example, by rivets 408, 410, 412 and 414 placed at the four corners of the front and back face plates 402 and 404. Alternative means for affixing the front and back plates together are well known. Thereafter, the sliding insert 406 is placed between the front and back face plates 402 and 404. Though not depicted in the figures, internal grooves guide the sliding insert 406 within the device 400.

With reference to FIG. 11, in an embodiment of the present invention, the ratio represents a mean aortic pressure (Pa) divided by a mean distal pressure (Pd) measured within a blood vessel. An upper slide-rule 420 includes a numerator scale 422, representing the Pa measurement, printed upon a face plate ranging from 1 to 40 mmHg. The upper slide-rule 420 also includes a denominator scale 424 (representing the Pd value) and calculated FFR scale 426 (Pa/Pd) printed upon the sliding insert 406 visible through a window 428 in the front face plate 402. The printed values upon the scales 422, 424 and 426 are logarithmic which facilitate the division through subtraction a value on the denominator scale 424 from a value on the numerator scale 422 and reading the result on the logarithmic calculated FFR scale 426.

An extended slide-rule 430 is provided to handle higher pressures in a range from 40 to 330 mmHg. In order to accommodate a greater range of aortic pressure readings, the lower scale is split into two portions. The arrangement of the extended slide-rule 430 scales corresponds to the arrangement described with reference to the upper slide-rule 420 scales. The Pa pressure values are printed on the front face plate 402. The Pd and calculated FFR values are printed upon the sliding insert 406. It is noted that this arrangement is modified so that the sheets upon which the scales are placed differs from those depicted, by way of example, in FIG. 11. Space permitting, instructions 440 for using the slide-rule device 400 are printed upon the front face plate 402. It should be noted that FFR may alternatively be digitally calculated and/or displayed.

Turning to FIG. 12, a set of charts is provided to assist decision-making after determining a patient's FFR for a particular vessel. A first section 460 provides a stent grading system based upon FFR values determined after performing balloon angioplasty and/or stent deployment. Values between 1.0 and 0.9 represent optimal results. FFR values between 0.9 and 0.75 characterize satisfactory results, but also carry a risk of restenosis. A value lower than 0.75 is characterized as unsatisfactory results (e.g., a significant lesion is still present).

A second section 470 provides guidance with regard to reading the results of FFR calculations. A first graph 472, labeled "Normal FFR Results" displays an example of an angiographically intermediate lesion. The pressure tracing displays that the lesion was assessed using a pressure guide wire, and the FFR was found to be above 0.75 (i.e. FFR=0.98). Thus, the lesion was not hemodynamically significant. The second graph labeled "Abnormal FFR Result" shows an example of an angiographically intermediate lesion that was assessed by a pressure wire, and the FFR pressure tracing result displayed was found to be less than 0.75. Therefore this lesion is hemodynamically significant and flow-limiting. A third section 480 provides set of study results relating FFR values, treatment, and event and survival rates of patients. It is noted that the following has been an example of the type of information that can be provided on the back face plate 404. In alternative embodiments of the invention, other information is provided.

A method of using apparatus of the present invention is now provided. With sensor 60 and physiology monitor 52 attached to signal conditioning device 50, sensor 60 is advanced to a target site within a patient's vasculature (not shown). A physiological parameter, for example, pressure, temperature, velocity, or flow volume, of blood flowing within the patient's blood vessel is measured with sensor 60 and sent to signal conditioning device 50. Device 50 conditions the signal and sends it to physiology monitor 52, which displays the signal as a measure of the physiological parameter at the target site. Measurements may be made at various locations within the patient's vessel to facilitate determination of medical treatment modalities appropriate for use at the target site. For example, if the treatment site comprises a stenosed region of the patient's vessel, sensor 60 may take pressure measurements across the stenosis for determination of fractional flow reserve, as described herein above with respect to FIGS. 11 and 12. Additional techniques will be apparent to those of skill in the art.

With reference to FIG. 13, an exemplary embodiment of a connector 500 constructed in accordance with a further aspect of the present invention is depicted. The connector 500 can be used to mechanically and electrically interconnect the guide wire 56 with the static cable 59 as shown in FIG. 2. The illustrated connector offers several significant advantages over known rotary connectors (see, e.g., U.S. Pat. Nos. 5,348,481 and 5,178,159) that have been used to provide connection to a guide wire. For example, the connector 500 is much easier to manipulate than known rotary connectors, which require an operator to pull and hold the nose back as the guide wire is being inserted. In addition to being awkward to manipulate, known rotary connectors require high insertion forces to place the guide wire in the connector. These high insertion forces can deceive an operator into erroneously believing that the guide wire is fully inserted. With the known rotary connectors, if the nose is released before the guide wire is fully inserted, the conductive bands on the guide wire can be crushed. In contrast, the connector 500 of the present invention requires very little insertion force to place the wire in the connector. While the present invention is described in connection with a guide wire 502 used in a pressure sensor-to-physiological monitor interface arrangement, those skilled in the art will appreciate that the connector can be used to mechanically and electrically interconnect any small diameter flexible elongate member having electrical capabilities to any electrical device.

As shown in FIGS. 13 and 15, the connector includes a generally cylindrical housing 504 which, in this case, has a two-piece construction. The two pieces can be joined by any suitable method such as by an adhesive or, more preferably, by snap-fit or press-fit. The housing 504 includes front and rear portions 506, 508 that are separated from each other by an annular shoulder 510. A nose piece 512 is arranged on the front end of the housing 504 with the nose piece 512 being supported for axial movement relative to the housing between open and closed positions. In the open position, the nose piece 512 is arranged in a forward position relative to the housing 504 such that a rear edge 514 of the nose piece is spaced forward of the annular shoulder 510 exposing a portion of the front portion 506 of the housing as shown in FIGS. 15-17. When the nose piece 512 is in the open position, a guide wire 502 can be freely inserted into the connector.

Figure 22:
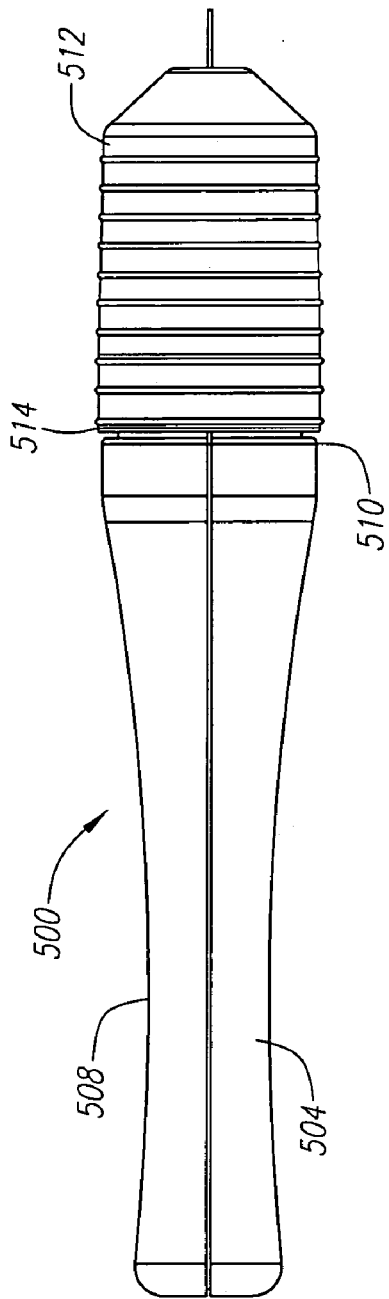
FIG. 22 is side elevation view of the connector of FIG. 13 showing the connector in the closed position.
Figure 23:
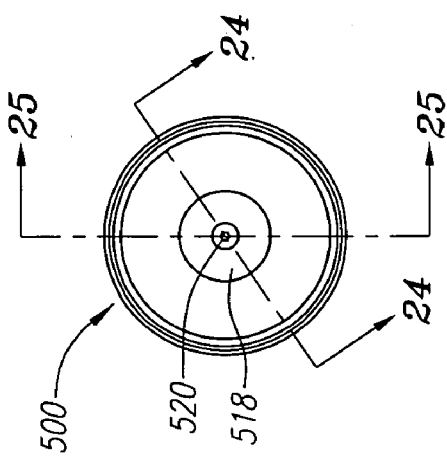
FIG. 23 is an end view of the connector of FIG. 22.

The nose piece 512 can be moved to the closed position by sliding the nose piece rearward relative to the housing 504 until the rear edge 514 of the nose piece is adjacent the annular shoulder 510 of the housing as shown in FIGS. 22, 24 and 25. In the closed position, the connector 500 establishes electrical contact between the guide wire 502 and the static cable and mechanically grips the guide wire so as to prevent the guide wire 502 from being withdrawn from the connector. A plurality of circumferential ridges 516 (FIGS. 13 and 15) are formed in the outer surface of the nose piece 512 to facilitate engagement of the nose piece by the fingers of an operator. Additionally, the illustrated housing 504 and nose piece 512 have an ergonomic shape which makes the connector 500 easier to handle and operate correctly. As will be appreciated, the housing 504 and nose piece 512 can be made of any suitable material, such as, for example, plastic.

In this instance, the rear end of the housing 504 is adapted to receive an end of the static cable while the guide wire is received through the front end of the housing 504 via the nose piece 512. Specifically, for receiving an end 517 of the guide wire 502, a countersink 518 is provided in the end of the nose piece 512 which tapers to an opening 520 through the end of the nose piece as best shown in FIG. 13. The opening 520 communicates with an axially extending internal bore 522 in the nose piece 512 that, in turn, opens into an axially extending bore 524 in the housing 504 (see, e.g., FIGS. 17 and 21). An insulator or carrier 526 is arranged in the internal bores 522, 524 in the nose piece 512 and housing 504 which defines an internal passage 527 for the guide wire 502 which is in axial alignment with the opening 520 in the end of the nose piece 512. To direct the guide wire 502 into the internal passage 527 the end of the carrier 526 arranged nearest the opening 520 in the nose piece 512 also includes a countersink portion 528.

To provide electrical connection to the guide wire 502, a plurality of contact members 530, in this case five, are supported by the carrier 526 in axially spaced relation as shown in FIG. 17. The contact members 530 are insulated from each other by the carrier 526 and are arranged along the guide wire passageway 527 defined by the carrier 526. In a known manner, the contact members are electrically connected to respective conductors in the static cable. In the illustrated embodiment, each contact member 530 includes a pair of opposing spring arms 532. A portion of each of the spring arms 532 extends outward through a corresponding opening 534 in the carrier 526. Each contact member 530 is configured and supported so as to move between engaged (see, e.g., FIG. 25) and disengaged (see, e.g., FIG. 17) positions with respect to a guide wire 502 arranged within the carrier 526.

For moving the contact members 530 between the engaged and disengaged positions as well as for mechanically clamping the guide wire 502, the connector 500 includes a pair of jaws 536 which are arranged in the internal bores 522, 524 of the nose piece 512 and housing 504 as shown in FIGS. 17 and 21. In particular, the jaws 536 are supported for movement between an open or released position (see, e.g., FIGS. 17 and 21) and a closed or clamped position (see, e.g., FIG. 25) in response to movement of the nose piece 512 between the open and closed positions. To this end, the jaws 536 are arranged in the internal bores 522, 524 of the nose piece and housing such that each jaw 536 extends generally axially relative to the nose piece 512 and housing 504 as shown in FIGS. 17 and 21. Each jaw 536 has an inner face 538 that faces the carrier 526 and that includes a plurality of axially spaced protrusions 540. In the released position, the inner faces 538 of the jaws 536 do not engage the carrier 526 with each jaw 536 being angled slightly radially outward as it extends towards the rear end of the connector 500 such that the space between the jaws 536 widens towards the rear ends of the jaws.

In the clamped position, the inner face 538 of each jaw 536 engages an opposing side of the carrier 526 with each protrusion 540 extending into a respective one of the openings 534 in the carrier and engaging the corresponding contact spring arm 532 as shown in FIG. 25. The engagement of each protrusion 540 on the inner face 538 of the jaw 536 with the respective contact spring arm 532 moves that contact member 530 into engagement with the guide wire 502 thereby establishing electrical contact. Additionally, the jaws 536 engage and grip the guide wire 502 when in the closed position so as to prevent withdrawal of the guide wire 502 from the connector 500. In the illustrated embodiment, the jaws 536 grip the guide wire 502 at a location near the front end of the jaws as shown by the reference number 542 in FIG. 25. To facilitate gripping of the guide wire 502 by the jaws 536, a grip tubing 544 is supported by the carrier 526 near the front end of the jaws so that the grip tubing 544 is in surrounding relation to the guide wire 502 inserted in the connector 500 (see, e.g., FIG. 16). When the jaws 536 are in the clamped position, the jaws pinch the grip tubing 544 into engagement with the guide wire 502 (see, e.g., FIG. 24). To this end, the grip tubing 544 is preferably made of a soft material.

To move the jaws 536 between the released and clamped positions, opposing cam surfaces 546 are provided on an inside surface of the internal bore 522 in the nose piece 512 as shown in FIGS. 17 and 21. Additionally, an outer face 548 of each jaw 536 defines a corresponding cam surface that tapers radially outward as it extends toward the rear end of the housing 504. Each jaw 536 is pivotally supported at or adjacent its front end so that as the nose piece 512 moves from the released to the clamped position, the cam surfaces 546 on the inside surface of the nose piece 512 push inwardly on the outer faces 548 of the jaws 536 and thereby pivot the jaws inwardly into their clamped positions (see, FIG. 25).

To ensure that a proper connection is established with the guide wire 502, an interlock mechanism is provided which prevents the nose piece 512 from being moved from the open to the closed position when the guide wire 502 is not fully inserted into the connector 500. Thus, the interlock mechanism also prevents the conductive bands on the guide wire 502 from being damaged by operation of the jaws 536 since the jaws cannot be moved to the closed position until the guide wire is fully inserted into the connector 500. In the illustrated embodiment, the interlock mechanism includes a plurality of locking pins 550 and a locking sleeve 552 which is supported in the internal bore 524 of the housing 504 for movement in the axial direction relative to the housing between locked (FIG. 16) and unlocked (FIG. 20) positions.

When the nose piece 512 is in the open position, the locking pins 550 engage a first set of notches 554 in the inner wall of the nose piece 512 near the rear edge 514 thereof as shown in FIG. 16. The locking pins 550 are supported so as to be deflectable in the radial inward direction. However, in the locked position, the sides 555 of the locking sleeve 552 are arranged directly radially inward of the locking pins 550 thereby blocking deflection of the locking pins. Since the locking pins 550 cannot deflect out of engagement with the notches 554, the nose piece 512 cannot be moved relative to the housing 504 into the closed position. In the unlocked position, the forward end of the locking sleeve 552 is arranged rearward of the locking pins 550 as shown in FIG. 20 such that the sides 555 of the locking sleeve 552 do not block the deflection of the locking pins. Thus, the nose piece 512 is free to move rearward relative to the housing 504 into the closed position as shown in FIG. 24.

The locking sleeve 552 moves between the locked and unlocked positions in response to movement of the guide wire 502 as the guide wire is inserted into the connector 500. In particular, when it nears a fully inserted position, the end of the guide wire 517 engages an end wall 556 of the locking sleeve 552 that is arranged a distance rearward of the jaws 536 and contact members 530. As the guide wire 502 continues moving the final short distance into its fully installed position, the guide wire 502 pushes the locking sleeve 552 rearward into the unlocked position as shown in FIG. 20. The movement of the locking sleeve 552 into the unlocked position is counter to the force of a compression spring 558 (FIGS. 17 and 21) that is arranged between a rear face of the end wall 556 of the locking sleeve 552 and a stop surface 560 in the housing 504. Thus, when the nose piece 512 is moved back into the open position and the guide wire 502 is removed from the connector 500, the spring 558 urges the locking sleeve 552 back into the locked position (see FIG. 16).

To insert a guide wire 502 into the connector 500, the nose piece 512 is first placed in the open position, which, in turn, opens the jaws 536 (see, e.g., FIG 17). Advantageously, the nose piece 512 is held in the open position by the interlock mechanism. In particular, as there is no guide wire 502 in engagement with the end wall 556 of the locking sleeve 552, the compression spring 558 urges the locking sleeve into the locked position thereby preventing movement of the nose piece 512 into the closed position as shown in FIG. 16. Thus, unlike conventional rotary connectors, there is no need for an operator to manually hold the nose piece 512 in the open position as the end of the guide wire 502 is inserted in the opening 520 in the front end of the nose piece. As a result, the connector 500 is much easier for an operator to manipulate during the guide wire insertion process.

As the guide wire 502 nears the fully inserted position, it engages the end wall 556 of the locking sleeve 552 and pushes the locking sleeve out from behind the locking pins 550 into the unlocked position (see FIG. 20). This disengages the locking pins 550 thereby allowing the nose piece 512 to be moved into the closed position as shown in FIGS. 24 and 25. Specifically, when the nose piece 512 is urged rearward relative to the housing 504 by an operator, the locking pins 550 deflect in a radially inward direction allowing the nose piece 512 to slide rearward. The movement of the nose piece 512 rearward towards the closed position urges the jaws 536 into the closed position. The closing movement of the jaws 536, in turn, brings the contact members 530 into engagement with the guide wire 502 and pinches the grip tubing 544 into engagement with the guide wire so as to secure the guide wire in the connector 500. As shown in FIG. 24, a second set of notches 562 are provided on the inside surface of the nose piece 512 which the locking pins 550 engage when the nose piece reaches the fully closed position. Since the guide wire 502 is secured in place by the jaws 536, the locking sleeve 552 is not allowed to slide back into the locked position.

To remove the guide wire 502 from the connector 500, the nose piece 512 is first pushed forward relative to the housing 504 into the open position as shown in FIGS. 16 and 17. This allows the jaws 536 to snap back via the force of a spring which extends between the two jaws into the open position thereby releasing the guide wire 502 such that it can be pulled out of the connector. Once the guide wire 502 has been removed, the compression spring 558 urges the locking sleeve 552 forward into the locked position behind the locking pins 550. This again locks the nose piece 512 in the open position.

Illustrative embodiments of the present invention and certain variations thereof have been provided in the Figures and accompanying written description. Those skilled in the art will readily appreciate from the above disclosure that many variations to the disclosed embodiment are possible in alternative embodiments of the invention. Such modifications include, by way of example, modifications to the form and/or content of the disclosed circuitry and functional blocks. The present invention is not intended to be limited to the disclosed embodiments. Rather the present invention is intended to cover the disclosed embodiments as well as others falling within the scope and spirit of the invention to the fullest extent permitted in view of this disclosure and the inventions defined by the claims appended herein below.

What is claimed is:

1. A connector for connecting a flexible elongate member having a sensor mounted thereon to a physiology monitor, the connector comprising:
   a housing having an internal passage therein;
   an electrical contact member disposed in the internal passage, the electrical contact member having a plurality of axially spaced contact members;
   a cable having a plurality of conductors, the plurality of conductors being electrically connected to respective axially spaced contact members;
   a sleeve having an opening therein which communicates with the internal passage in the housing and being moveable between an open position and a closed position;
   an interlock mechanism disposed in the housing having a locked position and an unlocked position, the interlock mechanism being in an unlocked position when an end of the flexible elongate member is fully inserted into the connector, the interlock mechanism being moveable between the locked position and the unlocked position by movement of the sleeve, wherein when the interlock mechanism is in the locked position, the sleeve is prevented from moving from the open to the closed position.

2. The connector of claim 1, wherein the flexible elongate member is a guide wire.

3. The connector of claim 1, wherein the sleeve is a nose piece.

4. A connector for connecting a flexible elongate member having a sensor mounted thereon to a physiology monitor, the connector comprising:
   a housing having an internal passage therein;

an engagement member disposed in the internal passage, the engagement member being moveable between an engaged position and a disengaged position, wherein the engagement member grips the flexible elongate member in the engaged position;

a sleeve having an opening therein which communicates with the internal passage in the housing and being moveable between an open position and a closed position, wherein when the sleeve is in the closed position, the engagement member is in the engaged position;

an interlock mechanism disposed in the housing having a locked position and an unlocked position, the interlock mechanism being in an unlocked position when an end of the flexible elongate member is fully inserted into the connector, the interlock mechanism being moveable between the locked position and the unlocked position by movement of the sleeve, wherein when the interlock mechanism is in the locked position, the sleeve is prevented from moving from the open to the closed position.

5. The connector of claim 4, wherein the flexible elongate member is a guide wire.

6. The connector of claim 4, wherein the sleeve is a nose piece.

7. A connector for connecting a flexible elongate member having a sensor mounted thereon to a physiology monitor, the connector comprising:

a housing having an internal passage therein;

an engagement member disposed in the internal passage, the engagement member being moveable between an engaged position and a disengaged position, wherein the engagement member grips the flexible elongate member in the engaged position;

a sleeve having an opening therein which communicates with the internal passage in the housing and being moveable between an open position and a closed position, wherein when the sleeve is in the closed position, the engagement member is in the engaged position;

an interlock mechanism disposed in the housing having a locked position and an unlocked position, the interlock mechanism being in an unlocked position when an end of the flexible elongate member is fully inserted into the connector, the interlock mechanism being moveable between the locked position and the unlocked position by movement of the sleeve, wherein when the interlock mechanism is in the locked position, the sleeve is prevented from moving from the open to the closed position; and grip tubing disposed in the housing and arranged coaxially around the flexible elongate member.

8. A connector for connecting a flexible elongate member having a sensor mounted thereon to a physiology monitor, the connector comprising:

a housing having an internal passage therein;

an electrical contact member disposed in the internal passage, the electrical contact member having a plurality of axially spaced contact members;

a cable having a plurality of conductors, the plurality of conductors being electrically connected to respective axially spaced contact members;

an engagement member disposed in the internal passage, the engagement member being moveable between an engaged position and a disengaged position, wherein the engagement member grips the flexible elongate member in the engaged position;

a sleeve having an opening therein which communicates with the internal passage in the housing and being moveable between an open position and a closed position, wherein when the sleeve is in the closed position, the engagement member is in the engaged position; and grip tubing disposed in the housing and arranged coaxially around the flexible elongate member.

9. A connector for connecting a flexible elongate member having a sensor mounted thereon to a physiology monitor, the connector comprising:

a housing having an internal passage therein;

a plurality of axially spaced contact members disposed in the internal passage of the housing, the plurality of contact members being moveable between engaged and disengaged positions with respect to the flexible elongate member;

a cable having a plurality of conductors, the plurality of conductors being electrically connected to respective contact members;

a sleeve having an opening therein which communicates with the internal passage in the housing and being moveable between an open position and a closed position, wherein movement of the sleeve between the open and closed positions causes movement of the plurality of contact members between the disengaged and engaged positions such that when the sleeve is in the open position the plurality of contact members are in the disengaged position and when the sleeve is in the closed position the plurality of contact members are in the engaged position; and a pair of engagement members disposed in the internal passage of the housing, the pair of engagement members being supported for movement between a released position and a clamped position in response to movement of the sleeve between the open and closed positions.

10. A connector for connecting a flexible elongate member having a sensor mounted thereon to a physiology monitor, the connector comprising:

a housing having an internal passage therein;

a plurality of axially spaced contact members disposed in the internal passage of the housing, the plurality of contact members being moveable between engaged and disengaged positions with respect to the flexible elongate member;

a cable having a plurality of conductors, the plurality of conductors being electrically connected to respective contact members;

a sleeve having an opening therein which communicates with the internal passage in the housing and being moveable between an open position and a closed position, wherein movement of the sleeve between the open and closed positions causes movement of the plurality of contact members between the disengaged and engaged positions such that when the sleeve is in the open position the plurality of contact members are in the disengaged position and when the sleeve is in the closed position the plurality of contact members are in the engaged position; and an interlock mechanism disposed in the housing for movement between a locked position and an unlocked position and being operable to move to the unlocked position when an end of the flexible elongate member reaches a fully inserted position in the connector, wherein in the locked position the interlock mechanism prevents movement of the sleeve from the open to the closed position.

* * * * *